US008911743B2

(12) United States Patent
Oliveira

(10) Patent No.: US 8,911,743 B2
(45) Date of Patent: Dec. 16, 2014

(54) *HAEMOPHILUS PARASUIS* POLYPEPTIDES AND METHODS OF USE

(75) Inventor: Simone Oliveira, New Brighton, MN (US)

(73) Assignee: Regents of the University of Minnesota, Saint Paul, MN (US)

( * ) Notice: Subject to any disclaimer, the term of this patent is extended or adjusted under 35 U.S.C. 154(b) by 0 days.

(21) Appl. No.: 13/508,225

(22) PCT Filed: Nov. 4, 2010

(86) PCT No.: PCT/US2010/055425
§ 371 (c)(1),
(2), (4) Date: Aug. 28, 2012

(87) PCT Pub. No.: WO2011/056954
PCT Pub. Date: May 12, 2011

(65) Prior Publication Data
US 2013/0129682 A1  May 23, 2013

Related U.S. Application Data

(60) Provisional application No. 61/257,921, filed on Nov. 4, 2009, provisional application No. 61/314,468, filed on Mar. 16, 2010.

(51) Int. Cl.
*A61K 39/00* (2006.01)
*A61K 39/102* (2006.01)
*C07K 1/00* (2006.01)
*G01N 33/569* (2006.01)
*C07K 14/285* (2006.01)

(52) U.S. Cl.
CPC ........ *C07K 14/285* (2013.01); *G01N 33/56911* (2013.01); *G01N 2333/285* (2013.01); *A61K 39/00* (2013.01); *A61K 2039/522* (2013.01); *G01N 2469/20* (2013.01); *A61K 2039/505* (2013.01)
USPC .................. 424/185.1; 424/190.1; 424/256.1; 530/350; 530/412

(58) Field of Classification Search
CPC .................. A61K 2039/505; A61K 2039/522; A61K 39/00; C07K 14/285; G01N 233/285
USPC .......... 424/185.1, 190.1, 256.1; 530/350, 412
See application file for complete search history.

(56) References Cited

U.S. PATENT DOCUMENTS

| | | | |
|---|---|---|---|
| 4,703,004 A | 10/1987 | Hopp et al. | |
| 4,782,137 A | 11/1988 | Hopp et al. | |
| 5,594,115 A | 1/1997 | Sharma | |
| 5,935,824 A | 8/1999 | Sgarlato | |
| 2010/0255035 A1* | 10/2010 | Oliveira et al. | 424/256.1 |

OTHER PUBLICATIONS

Zhou et al.,, Proteomics. May 2009;9(10):2722-39. A comprehensive proteome map of the *Haemophilus parasuis* serovar 5.*
Oliveira A et al Virulence-associated trimeric autotransporters of *Haemophilus parasuis* are antigenic proteins expressed in vivo Vet Res. May-Jun. 2010;41(3):26. Epub Dec. 10, 2009.*
Yue et al., J Bacteriol. Feb. 2009;191(4):1359-60. doi: 10.1128/JB.01682-08. Epub Dec. 12, 2008. Complete genome sequence of *Haemophilus parasuis* SH0165.*
Ngo, in the Protein Folding Problem and Tertiary Structure Prediction, Merz et al. (eds.), Birkhauser Boston: Boston, MA, pp. 433 and 492-495, 1994.*
Rudinger (in Peptide Hormones, Parsons (ed.), University Park Press: Baltimore, MD, pp. 1-7, 1976.*
Yue et al., J Bacteriol. Feb. 2009;191(4):1359-60. doi: 10.1128/JB.01682-08. Epub Dec. 12, 2008. Complete genome sequence of *Haemophilus parasuis* SH0165.*
Confer et al Am J Vet Res. Oct. 1996;57(10):1453-7. Antibody responses of cattle to outer membrane proteins of *Pasteurella multocida* A:3. Abstract.*
Bigas et al Development of a genetic manipulation system for *Haemophilus parasuis* Veterinary Microbiology vol. 105, Issues 3-4, Feb. 25, 2005, pp. 223-228.*
Nielsen; "Pathogenicity and immunity studies of *Haemophilus parasuis* serotypes"; Acta Veterinaria Scandinavica; vol. 34, No. 2, 1998, pp. 193-198; Abstract only.*
wikipedia.org/wiki/vertebrates, last visited Sep. 11, 2013.*
Bork et al Powers and Pitfalls in Sequence Analysis: The 70% Hurdle Genome Research 10:398-400.*
Angen et al., "Development of a species specific PCR test for detection of *Haemophilus parasuis*," *Veterinary Microbiology*, 2007; 119(2-4):266-276.
Beck et al., "Immunity and the Invertebrates," *Scientific American*, Nov. 1996; 60-66.
Berntsson et al., "The structural basis for peptide selection by the transport receptor OppA," *EMBO Journal*, 2009; 28(9):1332-1340.
Bowie et al., "Deciphering the message in protein sequences: tolerance to amino acid substitutions," *Science*, 1990; 247(4948):1306-1310.
Garmory et al., "ATP-Binding Cassette Transporters Are Targets for the Development of Antibacterial Vaccines and Therapies," *Infection and Immunology*, Dec. 2004; 72(12): 6757-6763.
Harlow et al., *Antibodies: A laboratory manual*, Cold Spring Harbor Laboratory Press, Cold Spring Harbor, 1988.

(Continued)

*Primary Examiner* — Maria Leavitt
(74) *Attorney, Agent, or Firm* — Mueting, Raasch & Gebhardt, P.A.

(57) ABSTRACT

The present invention provides isolated polypeptides having oligopeptide permease activity and an amino acid sequence that has at least 80% identity with a *Haemophilus parasuis* OppA polypeptide. Also provided by the present invention are isolated polynucleotides that encode the polypeptides described herein, and antibody that specifically binds a polypeptide described herein. The present invention further provides genetically modified microbes, such as attenuated *Haemophilus parasuis* strains and other microbes that express polypeptides described herein. Also included are methods for using the polypeptides, polynucleotides, antibody, and genetically modified microbes.

9 Claims, 12 Drawing Sheets

(56) References Cited

OTHER PUBLICATIONS

Heddle et al., "Crystal Structures of the Liganded and Unliganded Nickel-binding Protein NikA from *Escherichia coli*," *J. Biol. Chem.*, Dec. 2003; 278(50):50322-50329.
Higgins et al., "Periplasmatic protein associated with oligopeptide permeases of *Salmonella typhimurium* and *Escherichia coli*," *J. Bacteriol.*, 1983; 155(3):1434-1438.
Hoffmann et al., "The effect of a homologous bacterin given to sows prefarrowing on the development of Glässer's disease in postweaning pigs after i.v. challenge with *Haemophilus parasuis* serotype 5," *Dtsch. Tierarztl. Wochenschr.*, Jun. 2002; 109(6):271-276.
Hong et al., "Identification of novel immunogenic proteins in pathogenic *Haemophilus parasuis* based on genome sequence analysis," *Veterinary Microbiology*, Aug. 2011; 148:89-92.
Hong et al., "Table S1. List of selected *H. parasuis* potential vaccine candidates," *Veterinary Microbiology*, Aug. 2011; 148:1-3.
International Search Report issued Aug. 10, 2011, for International Patent Application No. PCT/US2010/055425, filed Nov. 4, 2010.
International Preliminary Report on Patentability issued May 8, 2012, in Switzerland, for International Patent Application No. PCT/US2010/055425, filed Nov. 4, 2010.
Monnet, "Bacterial oligopeptide-binding proteins," *Cell. Mol. Life Sci.*, 2003; 60:2100-2114.
National Center for Biotechnology Information, National Library of Medicine, National Institutes of Health, GenBank Locus ABY69417, Accession No. ABY69417, Version No. ABY69417.1 GI:165876369, "putative ABC transporter periplasmic binding protein [*Actinobacillus pleuropneumoniae* serovar 3 str. JL03" [online]. Bethesda, MD [retrieved on Aug. 23, 2013]. Retrieved from the Internet:<http://www.ncbi.nlm.nih.gov/protein/aby69417.1>; 2 pgs.
National Center for Biotechnology Information, National Library of Medicine, National Institutes of Health, GenBank Locus ACL32731, Accession No. ACL32731, Version No. ACL32731.1 GI:219691508, "ABC-type oligopeptide transport systems, periplasmic binding protein [*Haemophilus parasuis* SH0165]" [online]. Bethesda, MD [retrieved on Aug. 23, 2013]. Retrieved from the Internet:<http://www.ncbi.nlm.nih.gov/protein/acl32731>; 2 pgs.
National Center for Biotechnology Information, National Library of Medicine, National Institutes of Health, GenBank Locus CP000687, Accession No. CP000687, Version No. CP000687.1 GI:165875558, "*Actinobacillus pleuropneumoniae* serovar 3 str. JL03, complete genome" [online]. Bethesda, MD [retrieved on Aug. 23, 2013]. Retrieved from the Internet:<http://www.ncbi.nlm.nih.gov/nuccore/CP000687>; 274 pgs.
National Center for Biotechnology Information, National Library of Medicine, National Institutes of Health, GenBank Locus CP001321, Accession No. CP001321, Version No. CP001321.1 GI:219690483, "*Haemophilus parasuis* SH0165, complete genome" [online]. Bethesda, MD [retrieved on Aug. 23, 2013]. Retrieved from the Internet:<http://www.ncbi.nlm.nih.gov/nuccore/cp001321>; 314 pgs.
National Center for Biotechnology Information, National Library of Medicine, National Institutes of Health, GenBank Locus NC_010278, Accession No. NC_010278, Version No. NC_010278.1 GI:165975457, "*Actinobacillus pleuropneumoniae* serovar 3 str. JL03 chromosome, complete genome," [online]. Bethesda, MD [retrieved on Aug. 23, 2013]. Retrieved from the Internet:<http://www.ncbi.nlm.nih.gov/nuccore/clipboard>; 1 pg.
National Center for Biotechnology Information, National Library of Medicine, National Institutes of Health, GenBank Locus NC_011852, Accession No. NC_011852, Version No. NC_011852.1 GI:219870279, "*Haemophilus parasuis* SHO165 chromosome, complete genome," [online]. Bethesda, MD [retrieved on Aug. 23, 2013]. Retrieved from the Internet:<http://www.ncbi.nlm.nih.gov/nuccore/nc_011852.1>; 1 pg.
National Center for Biotechnology Information, National Library of Medicine, National Institutes of Health, GenBank Locus YP_002475067, Accession No. YP_002475067, Version No. YP_002475067.1 GI:219870692, "putative oligopeptide transporter, periplasmic-binding protein, OppA [*Haemophilus parasuis* SH0165]," [online]. Bethesda, MD [retrieved on Aug. 23, 2013]. Retrieved from the Internet:<http://www.ncbi.nlm.nih.gov/protein/yp_002475067.1>; 2 pgs.
Nowalk et al., "Serologic Proteome Analysis of *Borrelia burgdorferi* Membrane-Associated Proteins," *Infect. Immun.*, Jul. 2006; 74(7):3864-3873.
Oliveira, "*Haemophilus parasuis*: diagnosis, epidemiology, and control," Ph. D. thesis, University of Minnesota, St. Paul, Minnesota; 2003: 215 pgs.
Oliveira et al., "Characterization of the diversity of *Haemophilus parasuis* field isolates by use of serotyping and genotyping," *Am. J. Vet. Res.*, 2003; 64(4):435-442.
Oliveira et al., "Naturally-farrowed, artificially-reared pigs as an alternative model for experimental infection by *Haemophilus parasuis*," *Can. J. Vet. Res.*, 2003; 67(2):146-150.
Oliveira et al., "Evaluation of *Haemophilus parasuis* control in the nursery using vaccination and controlled exposure," *J. Swine Health and Production*, 2004; 12(3):123-128.
Oliveira et al., "*Haemophilus parasuis*: new trends on diagnosis, epidemiology and control," *Vet. Microbiol.*, Mar. 2004; 99(1):1-12.
Oliveira et al., "Safety of Controlled exposure to *Haemophilus parasuis*: the role of sow vaccination and PRRS virus infection," *Proceedings of the 18th International Pig Veterinary Congress*, Hamburg, Germany, 2004; p. 189.
Oliviera, Final Report, Dec. 1, 2009; 11 pgs.
Olvera et al., "Virulence-associated trimeric autotransporters of *Haemophilus parasuis* are antigenic proteins expressed in vivo," *Vet. Res.*, 2010; 5-6:41(3):26. Made available online Dec. 10, 2009.
Rozen et al., In: Krawetz and Misener (eds.), *Bioinformatics Methods and Protocols: Methods in Molecular Biology*, Humana Press, Totowa, NJ, 2000; pp. 365-386.
Ruiz et al., "Outer membrane proteins and DNA profiles in strains of *Haemophilus parasuis* recovered from systemic and respiratory sites," *J. Clin. Microbiol.*, 2001; 39(5):1757-62.
Sambrook et al., *Molecular Cloning: A Laboratory Manual*, Cold Spring Harbor Laboratory Press, 1989.
Sergeant, "Epitools epidemiological calculators,*AusVet Animal Health Services and Australian Biosecurity Cooperative Research Centre for Emerging Infectious Disease*," 2009; 1 pg. [Available online at http://epitools.ausvet.com.au/content.php?page=2Proportions].
Solano-Aguilar et al., "Protective role of maternal antibodies against *Haemophilus parasuis* infection," *Am. J. Vet. Res.*, 1999; 60(1):81-87.
Tame et al., "The structural basis of sequence-independent peptide binding by OppA protein," *Science*, Jun. 1994; 264(5165):1578-1581.
Tame et al., "The crystal structures of the oligopeptide-binding protein OppA complexed with tripeptide and tetrapeptide ligands," *Structure*, Dec. 1995; 3:1395-1406.
Tanabe et al., "The ABC transporter protein OppA provides protection against experimental *Yersinia pestis* infection," *Infect. Immun.*, Jun. 2006; 74(6):3687-3691.
Taverna et al., "Why Are Proteins So Robust to Site Mutations?" *J. Mol. Biol.* 2002; 315:479-484.
Tippayawat et al., "Phenotypic and Functional Characterization of Human Memory T Cell Responses to *Burkholderia pseudomallei*," *PLoS Negl. Trop. Dis.*, 2009; 3(4):e407.
Written Opinion issued May 4, 2012, in Germany, for International Patent Application No. PCT/US2010/055425, filed Nov. 4, 2010.
Yue et al., "Complete Genome Sequence of *Haemophilus parasuis* SH0165," *Journal of Bacteriology*, Feb. 2009; 191(4):1359-1360. Made available online on Dec. 12, 2008.
Yue et al., Uniprot Database Accession No. B8F5X9, Mar. 3, 2009; 1 pg.
Zhou et al., "A comprehensive proteome map of the *Haemophilus parasuis* serovar 5," *Proteomics*, May 2009; 9(10):2722-2739.
Zhou et al., "Identification and characterization of novel immunogenic outer membrane proteins of *Haemophilus parasuis* serovar 5," *Vaccine*, Aug. 2009; 27(38):5271-5277.

\* cited by examiner

Fig. 11A

```
SEQ ID:        10         20         30         40         50         60
    2    MTKHFEHNESRRGFMKLVAGVGAGLAFSGSIGTFASQAYAAPAKGSTIETGIAYPISTGF
         ::  ::  ::  :::  ::::  ::::::  ::::   :::    :  ::    ::    ::  ::::::::::
    4    MTSHFSHNDSRRHFMKLLAGVGAGFAFSGTLGTFSNNAFAAAGKG--IEAGIAYPISTGF
                    10         20         30         40         50

70         80         90        100        110        120
    2    DPMSSTGASSMAANIHIFEGLVDLHPATRQPYLALAAKEPEKVDDVTYRITLRDGAVFHN
         ::    :   :::::::::   :::::::::::::::::::::::::   :  :::  ::::   ::  ::
    4    DPLTSSGASSMAANLHIFEGLVDLHPATRQPYLALAAKEPEQKDEVTYHITLREGATFHD
              60         70         80         90        100        110

130        140        150        160        170        180
    2    GSAVTSADVVFSFERVLDPNTKSLFAQFIPFIKSVTAVDQKTVEFKLKYPFALFKERLTI
          :   ::   :::   ::::::::        ::::::::::  ::   :  : :   :::::::::::::::::::
    4    GKPVTTEDVVYSFERVLDPAKASLFAQFIPFIASVKALDNKVVEFKLKYPFALFKERLTI
             120        130        140        150        160        170

190        200        210        220        230        240
    2    IKIVPKALIEAQGQSVFDANPAGTGPYKFVSAVKDDRIVFEANPAYTGPYPATVEKMTWF
         :::::     ::   :::  :::    :  :   ::::::::::  ::::::::::::    :  :   :::   :  :::::
    4    VKIVPKHIVEA-GQSAFDAKPVGSGPYKFVSATKDDRIVFEANTSYNGMYPAKVDKMTWF
             180        190        200        210        220        230

250        260        270        280        290        300
    2    LLFDDAARVAAQESGRVQAIENVPYLDADRLKRKAAVESVQSFGLIFLMFNCEKAPFNNK
         ::  ::::::    ::::::::::::::    ::::::::  :::::    ::::::::::::::    :::::::::::::    :
    4    LLSDDAARVTAQESGRVQAIESVPYLDAERLKRKGKVESVQSFGLLFLMFNCEKAPFDNP
             240        250        260        270        280        290

310        320        330        340        350        360
    2    KVRQALQYAIDTQKLVDVVFLGNAKPATSYVQDSHPDYVKASTVYDFDPKKAAALLKEAG
         :::::::  :   :::::  :  :::::::::  :  :::::::::::  :  :::::::  ::::::::             ::::   ::   ::  :::
    4    KVRQALHYGLDTQKLIDIVFLGNAKAASSYVQDTHPDYVKAASQYDFDKAKAESLLAEAG
             300        310        320        330        340        350

370        380        390        400        410
    2    VDKLEFTTRSTAHKWVVDSVQMILEDWNKIPGVKVT--NIASQSPYNDGVDAGNFEVLIA
           :  :       :   :  ::         :::  ::        :::::         :    :      ::   :  :::  ::
    4    IKELKFELLATDHAWVKECAPLILESWNALKGVKVTLQHLQSGALYGTHVDKGAFEVVIA
             360        370        380        390        400        410

420        430        440        450        460        470
    2    PGDPSVFGNDLDLLLSWWYRGDVWPKKRFRWSNTPEYAEVQKLLDAAVAAKTPAEAREIW
         ::::::::::::::::::::::::::::  ::::  ::::::::::::::   :    ::  ::  :   ::  :
    4    PGDPSVFGNDLDLLLSWWYRGDVWPKRRFRWANTPEYAEVQKLLDEA--AKNPAGAKEAW
         420        430        440        450        460        470

480        490        500        510        520
    2    GKAINIIAEEAALYPIIHRKLPTAWSNKALDGFKPLSTTGMSFIGVSRK
         :::::::::     ::::  ::::::::::: :  :   :::   ::   ::  ::  ::
    4    TKAINIIAEQVPLYPIVHRKLPTAWSDKSLTDFQPLPTTGLSFLGVGRK
              480        490        500        510        520
```

Fig. 11B

SEQ ID NO:3

```
   1 atgacttctc attttctca taacgactca cgtcgccact tcatgaagct tcttgccggt
  61 gtcggagcag gctttgcatt ctccggtacc ttaggtactt tctctaataa tgcatttgcc
 121 gcagcaggta aaggtattga agcagggatt gcttatccga tctcaaccgg ttttgacccg
 181 cttacttcaa gcggtgcatc gtctatggcg gcgaacttac atatttttga aggtttagtg
 241 gatttacacc cggcaactcg ccaaccttat ttagctttag cggctaaaga gcctgaacag
 301 aaagatgaag taacatacca tattaccttg cgtgaagggg caaccttcca cgatggtaaa
 361 ccggttacca ccgaagatgt ggtttactcg tttgaacgtg tgttagatcc ggcgaaagcc
 421 tcactgttcg ctcaatttat tccgtttatc gcttcggtaa aagcacttga caataaagtg
 481 gtcgaattca aattaaaata tccgttcgct ttatttaaag aacgtttaac catcgtcaaa
 541 atcgtgccga acatatcgt agaagccggt caatccgcct tgatgccaa acctgtcggt
 601 tcaggtcctt ataaatttgt ttccgcaacc aaagatgacc gtattgtctt tgaagccaat
 661 acctcttata acggtatgta tccggctaaa gtagataaaa tgacgtggtt cttattatca
 721 gatgatgccg ctcgtgtaac cgcacaagaa tccggccgtg tacaagcgat tgaatccgta
 781 ccgtaccttg atgcggaacg cttaaaacgt aaaggaaaag tggaatcagt acaatctttc
 841 ggcttactat tcttaatgtt taactgtgaa aaagcaccgt ttgataaccc gaaagtacgc
 901 caggcgttac attatggctt agatacacaa aaattaatcg acattgtatt cttaggcaat
 961 gcgaaagcgg caagctctta cgtacaagat acccatcctg attatgtaaa agccgccagc
1021 caatatgatt tgataaagc gaaagcggaa agcctattag cggaagcggg tatcaaagaa
1081 ttaaaatttg aattacttgc aaccgatcac gcttgggtaa aagaatgtgc gccgcttatt
1141 cttgaatctt ggaatgcgtt aaaaggtgtg aaagtaacgc ttcaacattt acaatccggt
1201 gcgttatacg gcacgcacgt tgataaaggt gcgtttgaag tggttatcgc accgggcgat
1261 ccgtccgtat tcggtaacga cttagactta ttattaagct ggtggtaccg cggtgacgta
1321 tggccgaaac gtcgtttccg ttgggcaaat acgcctgaat atgccgaagt acaaaaatta
1381 ctggatgaag cggcgaaaaa tccggcgggt gcaaaagaag catggaccaa agcaatcaat
1441 attattgccg aacaagtgcc gctttacccg atcgtgcatc gtaaattacc gaccgcatgg
1501 agcgataaat cacttaccga tttccaaccg ttaccgacaa caggcttgtc attcttaggc
1561 gtcggtcgta aataa
```

Fig. 12

```
SEQ
 2    MTKHFEHNESRRGFMKLVAGVGAGLAFSGSIGTFASQAYAAPAKGSTIET
 5    MKTQFELNESRRHFMKLLAGASAGLAFSGTLGTFSAEAFASAPAGSSIEA
 4    MTSHFSHNDSRRHFMKLLAGVGAGFAFSGTLGTFSNNAFAAAGKG--IEA
 6    MKKQFEHNESRRGFMKLIAGVGAGMAFSGTLGTFTPKAFAAPAAGSTIEA
       *  * *** **** **  ** ****  ***   * *    *  **

GIAYPISTGFDPMSSTGASSMAANIHIFEGLVDLHPATRQPYLALAAKEP
      GIAYPISTGFDPLTASGASSQAANLHIFEGLVDLHPATRQPYLALAAKDP
      GIAYPISTGFDPLTSSGASSMAANLHIFEGLVDLHPATRQPYLALAAKEP
      GIAYPISTGFDPLTSSGASSMAANLHIFEGLVDLHPATRKPYLALAAEP
      ************    ****  *** ************** *******  *

EKVDDVTYRITLRDGAVFHNGSAVTSADVVFSFERVLDPNTKSLFAQFIP
      EMKDDVTYHVTLRDGAVFHDGKPVTTEDVVYSFERVLDPAKASLFAQFIP
      EQKDEVTYHITLREGATFHDGKPVTTEDVVYSFERVLDPAKASLFAQFIP
      EKIDDVTYRITLRDGAKFHNGNPVTTEDVVYSFERVLDPAKASLFAQFIP
      *  * ***  *** ** **  *   ** *** ********  ********

FIKSVTAVDQKTVEFKLKYPFALFKERLTIIKIVPKALIEAQGQSVFDAN
      FIESVKALDDKVVEFKLKYPFALFKERLTIVKIVPKHIVEA-GQSAFDAN
      FIASVKALDNKVVEFKLKYPFALFKERLTIVKIVPKHIVEA-GQSAFDAK
      FIDTVKKVDDKVVEFKLKYPFALFKERLTIVKIVPKAVVEA-GQAAFDAN
      **  *    * * *****************  *****   ** **   ***

PAGTGPYKFVSAVKDDRIVFEANPAYTGPYPATVEKMTWFLLFDDAARVA
      PIGSGPYRFVSATKDDRIVFAANPAYNGIYPAKVEKMTWFLLADDAARVT
      PVGSGPYKFVSATKDDRIVFEANTSYNGMYPAKVDKMTWFLLSDDAARVT
      PVGTGPYKFVSATKDDRIVFEAFADYNGGYPAQVEKMTWFLLSDDAARVT
      *  * *** **** *******  *    *  * *** * ******* ******

AQESGRVQAIENVPYLDADRLKRKAAVESVQSFGLIFLMFNCEKAPFNNK
      AQESGRIQAMESVPYLDAQRLKRKTEVQPVQSFGLLFLMFNCEKAPFNNP
      AQESGRVQAIESVPYLDAERLKRKGKVESVQSFGLLFLMFNCEKAPFDNP
      AQESGRVQAIESVPYLDAERLKRKGTVESVQSFGLLFLMFNCEKAPFNNP
      ****** ** * ****** *****   *  ***** *********** *
```

Fig. 12 (cont.)

```
KVRQALQYAIDTQKLVDVVFLGNAKPATSYVQDSHPDYVKASTVYDFDPK
KVRQALHYAIDTQKLIDIAFLGNAKAATSYVQDTHPDYVKATSQYDFDKA
KVRQALHYGLDTQKLIDIVFLGNAKAASSYVQDTHPDYVKAASQYDFDKA
KVRQALHYGLDTQKLIDVVFLGNAKAATSYVQDTHPDYVKANSQYDFDKA
******  *  *****  *  ******  *  ***** ******    ****

KAAALLKEAGVDKLEFTTRSTAHKWVVDSVQMILEDWNKIPGVKVTNIAS
KAEALLKEAGVTELKFQLLSTDHTWVKECAPLILESWNALKGVKATLQHL
KAESLLAEAGIKELKFELLATDHAWVKECAPLILESWNALKGVKVTLQHL
KAEALLAEAGVTELKFELLATDHSWVKECAPLILESWNSLKGVKVSLKHL
**  ** ***    * *   * * **        *** **    ***

QS--PYNDGVDAGNFEVLIAPGDPSVFGNDLDLLLSWWYRGDVWPKKRFR
QSGALYGAHVDKGNFEVVIAPGDPSVFGNDLDLLLSWWYRGDVWPKRRFR
QSGALYGTHVDKGAFEVVIAPGDPSVFGNDLDLLLSWWYRGDVWPKRRFR
QSGALYGTHVDKGAYEVVIAPGDPSVFGNDLDLLLSWWYRGDVWPKRRFR
**     *   **  *  ** ***************************  ***

WSNTPEYAEVQKLLDAAVAAKTPAEAREIWGKAINIIAEEAALYPIIHRK
WSNTPEYAEVQKLLDEAVRAKSHEEAKTAWTKAINIIAEQVPLYPIIHRK
WANTPEYAEVQKLLDEAA--KNPAGAKEAWTKAINIIAEQVPLYPIVHRK
WSETAEYAEVQKLLDEAA--KNPAASKEAWAKAINIIAEQVPLYPIIHRK
*  *  *********  *     *        * ********   **** ***

LPTAWSNKALDGFKPLSTTGMSFIGVSRK-
LPTAWNAKALTDFQPLPTTGLSFLGVGRK-
LPTAWSDKSLTDFQPLPTTGLSFLGVGRK-
LPTAWNDKALTGFQPLPTTGMSFIGVGRAK
*****  *  *   * **  ***  ** **  *
```

Fig. 13

1. Subclone 81133-1(ABC-type oligopeptide transport systems ATP-bindi) into pGSC3

Translation (His + TEV + ABC-type oligopeptide transport systems ATP-bindi)

Protein Length=550    MW=60754.4    Predicted pI=8.34

```
1     MNHKVHHHHH HMELGTENLYFQGMTKHFEH NESRRGFMKL VAGVGAGLAF SGSIGTFASQ
61    AYAAPAKGST IETGIAYPIS TGFDPMSSTG ASSMAANIHI FEGLVDLHPA TRQPYLALAA
121   KEPEKVDDVT YRITLRDGAV FHNGSAVTSA DVVFSFERVL DPNTKSLFAQ FIPFIKSVTA
181   VDQKTVEFKL KYPFALFKER LTIIKIVPKA LIEAQGQSVF DANPAGTGPY KFVSAVKDDR
241   IVFEANPAYT GPYPATVEKM TWFLLFDDAA RVAAQESGRV QAIENVPYLD ADRLKRKAAV
301   ESVQSFGLIF LMFNCEKAPF NNKKVRQALQ YAIDTQKLVD VVFLGNAKPA TSYVQDSHPD
361   YVKASTVYDF DPKKAAALLK EAGVDKLEFT TRSTAHKWVV DSVQMILEDW NKIPGVKVTN
421   IASQSPYNDG VDAGNFEVLI APGDPSVFGN DLDLLLSWWY RGDVWPKKRF RWSNTPEYAE
481   VQKLLDAAVA AKTPAEAREI WGKAINIIAE EAALYPIIHR KLPTAWSNKA LDGFKPLSTT
541   GMSFIGVSRK
```

2. Subclone 81133-1(ABC-type oligopeptide transport systems ATP-bindi) into pGSE4

Translation (His + EK + ABC-type oligopeptide transport systems ATP-bindi)

Protein Length=685    MW=74992.8    Predicted pI=6.77

```
1     MSDKIIHLTD DSFDTDVLKA DGAILVDFWA EWCGPCKMIA PILDEIADEY QGKLTVAKLN
61    IDQNPGTAPK YGIRGIPTLL LFKNGEVAAT KVGALSKGQL KEFLDANLAG SGSGHMHHHH
121   HHSSGLVPRG SGMKETAAAK FERQHMDSPD LGTDDDDKMT KHFEHNESRR GFMKLVAGVG
181   AGLAFSGSIG TFASQAYAAP AKGSTIETGI AYPISTGFDP MSSTGASSMA ANIHIFEGLV
241   DLHPATRQPY LALAAKEPEK VDDVTYRITL RDGAVFHNGS AVTSADVVFS FERVLDPNTK
301   SLFAQFIPFI KSVTAVDQKT VEFKLKYPFA LFKERLTIIK IVPKALIEAQ GQSVFDANPA
361   GTGPYKFVSA VKDDRIVFEA NPAYTGPYPA TVEKMTWFLL FDDAARVAAQ ESGRVQAIEN
421   VPYLDADRLK RKAAVESVQS FGLIFLMFNC EKAPFNNKKV RQALQYAIDT QKLVDVVFLG
481   NAKPATSYVQ DSHPDYVKAS TVYDFDPKKA AALLKEAGVD KLEFTTRSTA HKWVVDSVQM
541   ILEDWNKIPG VKVTNIASQS PYNDGVDAGN FEVLIAPGDP SVFGNDLDLL LSWWYRGDVW
601   PKKRFRWSNT PEYAEVQKLL DAAVAAKTPA EAREIWGKAI NIIAEEAALY PIIHRKLPTA
661   WSNKALDGFK PLSTTGMSFI GVSRK
```

3. Sub-clone 81133-1(ABC-type oligopeptide transport systems ATP-bindi) into pGS 21a Translation (His + EK + ABC-type oligopeptide transport systems ATP-bindi)

Protein Length=775    MW=86625.7    Predicted pI=7.13

```
1     MSGSHHHHHH SSGMSPILGY WKIKGLVQPT RLLLEYLEEK YEEHLYERDE GDKWRNKKFE
61    LGLEFPNLPY YIDGDVKLTQ SMAIIRYIAD KHNMLGGCPK ERAEISMLEG AVLDIRYGVS
121   RIAYSKDFET LKVDFLSKLP EMLKMFEDRL CHKTYLNGDH VTHPDFMLYD ALDVVLYMDP
181   MCLDAFPKLV CFKKRIEAIP QIDKYLKSSK YIAWPLQGWQ ATFGGGDHPP KSDLGHTGHR
241   SGTDDDDKMT KHFEHNESRR GFMKLVAGVG AGLAFSGSIG TFASQAYAAP AKGSTIETGI
301   AYPISTGFDP MSSTGASSMA ANIHIFEGLV DLHPATRQPY LALAAKEPEK VDDVTYRITL
361   RDGAVFHNGS AVTSADVVFS FERVLDPNTK SLFAQFIPFI KSVTAVDQKT VEFKLKYPFA
421   LFKERLTIIK IVPKALIEAQ GQSVFDANPA GTGPYKFVSA VKDDRIVFEA NPAYTGPYPA
481   TVEKMTWFLL FDDAARVAAQ ESGRVQAIEN VPYLDADRLK RKAAVESVQS FGLIFLMFNC
541   EKAPFNNKKV RQALQYAIDT QKLVDVVFLG NAKPATSYVQ DSHPDYVKAS TVYDFDPKKA
601   AALLKEAGVD KLEFTTRSTA HKWVVDSVQM ILEDWNKIPG VKVTNIASQS PYNDGVDAGN
661   FEVLIAPGDP SVFGNDLDLL LSWWYRGDVW PKKRFRWSNT PEYAEVQKLL DAAVAAKTPA
721   EAREIWGKAI NIIAEEAALY PIIHRKLPTA WSNKALDGFK PLSTTGMSFI GVSRK
```

Fig. 14

SEQ ID NO:9

```
ATGACCAAACATTTCGAACACAACGAATCTCGTCGCGGTTTTATGAAACTGGTGGCGGGTGTTGGTGCAGGTCTGGC
ATTCTCTGGTAGTATCGGCACCTTTGCCTCTCAGGCGTATGCGGCCCCGGCCAAAGGTAGTACCATTGAAACGGGCA
TCGCATACCCGATTAGCACCGGTTTCGATCCGATGAGCTCTACGGGCGCCAGTAGCATGGCAGCGAATATTCATATC
TTTGAAGGCCTGGTGGATCTGCACCCGGCAACCCGTCAGCCGTATCTGGCACTGGCCGCAAAAGAACCGGAAAAAGT
GGATGATGTTACCTACCGTATTACGCTGCGCGATGGTGCGGTGTTTCATAACGGCTCTGCGGTTACCAGTGCCGATG
TGGTTTTTAGCTTCGAACGCGTTCTGGACCCGAATACGAAATCTCTGTTTGCGCAGTTCATTCCGTTTATCAAAAGT
GTGACCGCCGTTGATCAGAAAACGGTGGAATTCAAACTGAAATATCCGTTCGCGCTGTTTAAAGAACGTCTGACCAT
TATCAAAATCGTGCCGAAAGCACTGATTGAAGCGCAGGGTCAGAGTGTTTTTGATGCAAACCCGGCAGGCACCGGTC
CGTACAAATTCGTGAGCGCCGTTAAAGATGATCGCATCGTGTTTGAAGCAAATCCGGCGTATACGGGTCCGTACCCG
GCAACCGTTGAAAAAATGACGTGGTTCCTGCTGTTTGATGATGCAGCCCGTGTGGCAGCACAGGAAAGCGGTCGTGT
GCAGGCAATTGAAAACGTTCCGTATCTGGATGCGGATCGTCTGAAACGCAAAGCCGCAGTGGAAAGTGTTCAGAGCT
TCGGTCTGATCTTCCTGATGTTTAATTGCGAAAAAGCCCCGTTTAACAATAAAAAAGTGCGTCAGGCCCTGCAGTAT
GCAATTGATACCCAGAAACTGGTTGATGTGGTTTTTCTGGGCAACGCCAAACCGGCAACCAGCTACGTGCAGGATTC
TCATCCGGATTATGTGAAAGCGAGCACGGTTTACGATTTCGATCCGAAAAAAGCGGCCGCACTGCTGAAAGAAGCAG
GTGTTGATAAACTGGAATTTACCACGCGCAGTACCGCGCACAAATGGGTGGTTGATAGCGTGCAGATGATCCTGGAA
GATTGGAACAAAATTCCGGGCGTGAAAGTTACGAATATCGCGAGCCAGTCTCCGTATAACGATGGTGTGGATGCGGG
CAATTTCGAAGTTCTGATTGCCCCGGGTGATCCGAGCGTTTTTGGCAACGATCTGGATCTGCTGCTGTCTTGGTGGT
ATCGTGGCGATGTGTGGCCGAAAAAAACGTTTTCGCTGGAGCAATACCCCGGAATACGCGGAAGTGCAGAAACTGCTG
GATGCGGCCGTTGCAGCGAAAACGCCGGCGGAAGCCCGTGAAATCTGGGTAAAGCGATTAACATTATCGCCGAAGA
AGCCGCACTGTATCCGATTATCCACCGCAAACTGCCGACCGCATGGAGCAATAAAGCGCTGGATGGCTTCAAACCGC
TGAGTACCACGGGTATGAGCTTTATTGGCGTGTCTCGCAAA
```

HAEMOPHILUS PARASUIS POLYPEPTIDES AND METHODS OF USE

CROSS-REFERENCE TO RELATED APPLICATIONS

This application is a U.S. National Stage Application of International Application No. PCT/US2010/055425, titled HAEMOPHILUS PARASUIS POLYPEPTIDES AND METHODS OF USE, filed on Nov. 4, 2010, published in the English language on May 12, 2011 as International Publication No. WO 2011/056954 A2, which claims the benefit of U.S. Provisional Application Ser. No. 61/257,921, filed Nov. 4, 2009, and U.S. Provisional Application Ser. No. 61/314,468, filed Mar. 16, 2010, each of which is incorporated by reference herein.

BACKGROUND

Haemophilus parasuis is an important cause of mortality in nursery pigs (Oliveira and Pijoan, 2004, Vet. Microbiol., 99(1):1-12). It is a commensal organism that colonizes virtually 100% of swine herds worldwide, and a frequent opportunistic pathogen during concurrent viral infections and stressful events (Oliveira et al., 2004, Safety of Controlled exposure to Haemophilus parasuis: the role of sow vaccination and PRRS virus infection. Proceedings of the 18th International Pig Veterinary Congress, Hamburg, Germany, p. 189), causing up to 60% mortality in naïve populations.

Protection against H. parasuis systemic infection is associated with the presence of antibodies against this pathogen (Solano-Aguilar et al., 1999, Am. J. Vet. Res., 60(1):81-87). The high susceptibility of colostrum-deprived pigs to H. parasuis systemic infection corroborates the importance of maternal antibodies as a major defense mechanism against this agent (Oliveira et al., 2003, Can. J. Vet. Res., 67(2):146-150). Commercial and autogenous vaccines currently available for H. parasuis generally do not provide complete cross-protection among different strains and serotypes due to extensive genotypic and phenotypic variation between different H. parasuis strains (Oliveira et al., 2003, Am. J. Vet. Res., 64(4):435-442, Oliveira et al., 2004, J. Swine Health and Production, 12(3):123-128). This is a major limitation to preventing nursery mortality against this pathogen. Antibiotics can be useful in controlling H. parasuis outbreaks; however, like other modern food-animal based industries, the swine industry is rapidly reducing the use of antibiotics to control mortality.

SUMMARY OF THE INVENTION

Haemophilus parasuis continues to be one of the most important causes of nursery mortality in modern swine production. Challenges in H. parasuis control include the lack of a reliable serological test to characterize the development of antibodies in sows and piglets, and the absence of vaccine that acts to suppress disease caused by H. parasuis. As described herein, a highly immunogenic and species-specific protein has been identified in H. parasuis. This protein was not only present in H. parasuis strains causing outbreaks, but was also present in reference strains representing 13 different serotypes. The convalescent serum that detected this protein did not detect a similar antigen in 10 other closely related bacterial swine pathogens tested, confirming that this protein was highly specific for H. parasuis. The highly immunogenic protein was identified as the oligopeptide permease A (OppA), which is a component of the ATP-binding cassette (ABC) transporter system in H. parasuis. Testing of serum samples obtained from non-clinical, clinical, and convalescent pigs suggested that colonized healthy pigs do not respond to this protein, whereas survivor pigs generated high titers against H. parasuis OppA.

The present invention provides isolated polynucleotides. The polynucleotides encode a polypeptide having oligopeptide permease activity, or a fragment thereof. In one embodiment the amino acid sequence of the polypeptide has at least 80% identity with SEQ ID NO:2. In another embodiment, the nucleotide sequence of the polynucleotide has at least 80% identity with SEQ ID NO:1. The full complement of the polynucleotides are also included in the present invention. The polynucleotides may include a heterologous polynucleotide, such as a regulatory sequence or a vector.

Also provided by the present invention are isolated polypeptides. The polypeptides have oligopeptide permease activity, and an amino acid sequence that has at least 80% identity with SEQ ID NO:2. Also included in the present invention are fragments of the polypeptides, and such fragments may have oligopeptide permease activity. The polypeptides may include a heterologous polypeptide.

The present invention further provides genetically modified microbes. The genetically modified microbes may include an exogenous polynucleotide, wherein the exogenous polynucleotide is a polynucleotide of the present invention. A genetically modified microbe may be E. coli. A genetically modified microbe of the present invention may be a Haemophilus parasuis. Such a genetically modified Haemophilus parasuis may include an oppA coding region that contains a mutation, such as a point mutation, a deletion, an insertion, or a combination thereof. The polypeptide encoded by the oppA coding region may have oligopeptide permease activity, and in other embodiments may not have oligopeptide permease activity. In one embodiment the oppA coding region does not encode a polypeptide. In some embodiments the genetically modified Haemophilus parasuis has decreased virulence in a pig.

Also included in the present invention is antibody that specifically binds a polypeptide having SEQ ID NO:2, wherein the antibody does not bind to a polypeptide that has an amino acid sequence SEQ ID NO:4. The antibody may be present in a composition that includes a pharmaceutically acceptable carrier. In one embodiment the antibody is a monoclonal antibody. The present invention also provides methods for making an antibody. The method may include administering to an animal a polypeptide in an amount effective to cause the production of an antibody specific for the polypeptide, where the polypeptide includes an amino acid sequence having at least 80% identity with SEQ ID NO:2 and has oligopeptide permease activity. The method may include isolating the antibody.

The present invention provides methods for detecting antibody. The method may include mixing a biological sample from an animal with a polypeptide under conditions suitable for formation of a polypeptide:antigen complex between antibody present in the biological sample and the polypeptide, where the polypeptide includes an amino acid sequence having at least 80% identity with SEQ ID NO:2 and has oligopeptide permease activity. The polypeptide may be bound to a surface. The method may include detecting the complex, where the presence of the complex indicates the animal has antibody that specifically binds to the polypeptide. Detecting the complex may include contacting the antibody with a secondary antibody, such as a secondary antibody that includes a detectable label. The presence of the complex may indicate the animal has been infected with Haemophilus

*parasuis*. The biological sample may include serum, oral fluid, colostrum, lung lavage, bronchial lavage, tracheal lavage, or nasal lavage. The biological sample may be from a pig.

In another embodiment, the method may include mixing a biological sample from an animal with an antibody under conditions suitable for formation of a polypeptide:antigen complex between a polypeptide present in the biological sample and the antibody, where the antibody specifically binds a polypeptide having an amino acid SEQ ID NO:2. The antibody may be bound to a surface. The method may include detecting the complex, where the presence of the complex indicates the biological sample includes a *Haemophilus parasuis* OppA polypeptide. Detecting the complex may include contacting the polypeptide with a secondary antibody, such as a secondary antibody that includes a detectable label. The presence of the complex may indicate the animal has been infected with *Haemophilus parasuis*. The biological sample may include serum, oral fluid, colostrum, lung lavage, bronchial lavage, tracheal lavage, or nasal lavage. The biological sample may be from a pig.

Further provided by the present invention are methods for detecting the presence of a *Haemophilus parasuis*. Such methods may include amplifying a target polynucleotide by contacting the target polynucleotide with a primer pair under suitable conditions to result in an amplified product, wherein the primer pair amplifies a target nucleotide including SEQ ID NO:1 and does not amplify a target nucleotide including SEQ ID NO:3, and detecting the amplified product, wherein the presence of the amplified product is indicative of the presence of a *Haemophilus parasuis*. The target polynucleotide may be present in a biological sample.

The present invention also provides methods for treating an animal at risk of infection with a *Haemophilus parasuis*. The methods may include administering to the animal a composition that includes an attenuated *Haemophilus parasuis*, where the attenuated *Haemophilus parasuis* includes a mutation in an oppA coding region or an operably linked regulatory region, and wherein the *Haemophilus parasuis* has decreased virulence in a pig when compared to the same *Haemophilus parasuis* having a wild-type oppA coding region.

Also provided by the present invention are methods for treating an animal at risk of infection with a *Haemophilus parasuis*. The methods may include administering to the animal a composition that includes a polypeptide or a fragment thereof, wherein the amino acid sequence of the polypeptide has at least 80% identity to the amino acid sequence of SEQ ID NO: 2, and wherein the polypeptide has oligopeptide permease activity.

As used herein, the term "polynucleotide" refers to a polymeric form of nucleotides of any length, either ribonucleotides or deoxynucleotides, and includes both double- and single-stranded RNA and DNA. A polynucleotide can be obtained directly from a natural source, or can be prepared with the aid of recombinant, enzymatic, or chemical techniques. A polynucleotide can be linear or circular in topology. A polynucleotide may be, for example, a portion of a vector, such as an expression or cloning vector, or a fragment. A polynucleotide may include nucleotide sequences having different functions, including, for instance, coding regions, and non-coding regions such as regulatory regions.

As used herein, the terms "coding region" and "coding sequence" are used interchangeably and refer to a nucleotide sequence that encodes a polypeptide and, when placed under the control of appropriate regulatory sequences expresses the encoded polypeptide. The boundaries of a coding region are generally determined by a translation start codon at its 5' end and a translation stop codon at its 3' end. A "regulatory sequence" is a nucleotide sequence that regulates expression of a coding sequence to which it is operably linked. Non-limiting examples of regulatory sequences include promoters, enhancers, transcription initiation sites, translation start sites, translation stop sites, and transcription terminators. The term "operably linked" refers to a juxtaposition of components such that they are in a relationship permitting them to function in their intended manner. A regulatory sequence is "operably linked" to a coding region when it is joined in such a way that expression of the coding region is achieved under conditions compatible with the regulatory sequence.

A polynucleotide that includes a coding region may include heterologous nucleotides that flank one or both sides of the coding region. As used herein, "heterologous nucleotides" refer to nucleotides that are not normally present flanking a coding region that is present in a wild-type cell. For instance, a coding region present in a wild-type microbe and encoding a polypeptide is flanked by homologous sequences, and any other nucleotide sequence flanking the coding region is considered to be heterologous. Examples of heterologous nucleotides include, but are not limited to regulatory sequences. Typically, heterologous nucleotides are present in a polynucleotide of the present invention through the use of standard genetic and/or recombinant methodologies well known to one skilled in the art. A polynucleotide of the present invention may be included in a suitable vector. The presence of heterologous nucleotides flanking one or both sides of a polynucleotide described herein result from human manipulation.

As used herein, an "exogenous polynucleotide" refers to a polynucleotide that is not normally or naturally found in a microbe. As used herein, the term "endogenous polynucleotide" refers to a polynucleotide that is normally or naturally found in a microbe. An "endogenous polynucleotide" is also referred to as a "native polynucleotide."

The terms "complement" and "complementary" as used herein, refer to the ability of two single stranded polynucleotides to base pair with each other, where an adenine on one strand of a polynucleotide will base pair to a thymine or uracil on a strand of a second polynucleotide and a cytosine on one strand of a polynucleotide will base pair to a guanine on a strand of a second polynucleotide. Two polynucleotides are complementary to each other when a nucleotide sequence in one polynucleotide can base pair with a nucleotide sequence in a second polynucleotide. For instance, 5'-ATGC and 5'-GCAT are complementary. The term "substantial complement" and cognates thereof as used herein, refer to a polynucleotide that is capable of selectively hybridizing to a specified polynucleotide under stringent hybridization conditions. Stringent hybridization can take place under a number of pH, salt and temperature conditions. The pH can vary from 6 to 9, preferably 6.8 to 8.5. The salt concentration can vary from 0.15 M sodium to 0.9 M sodium, and other cations can be used as long as the ionic strength is equivalent to that specified for sodium. The temperature of the hybridization reaction can vary from 30° C. to 80° C., preferably from 45° C. to 70° C. Additionally, other compounds can be added to a hybridization reaction to promote specific hybridization at lower temperatures, such as at or approaching room temperature. Among the compounds contemplated for lowering the temperature requirements is formamide. Thus, a polynucleotide is typically substantially complementary to a second polynucleotide if hybridization occurs between the polynucleotide and the second polynucleotide. As used herein, "specific hybridization" refers to hybridization between two polynucleotides under stringent hybridization conditions.

As used herein, the term "polypeptide" refers broadly to a polymer of two or more amino acids joined together by peptide bonds. The term "polypeptide" also includes molecules which contain more than one polypeptide joined by a disulfide bond, or complexes of polypeptides that are joined together, covalently or noncovalently, as multimers (e.g., dimers, tetramers). Thus, the terms peptide, oligopeptide, enzyme, and protein are all included within the definition of polypeptide and these terms are used interchangeably. It should be understood that these terms do not connote a specific length of a polymer of amino acids, nor are they intended to imply or distinguish whether the polypeptide is produced using recombinant techniques, chemical or enzymatic synthesis, or is naturally occurring.

As used herein, "oligopeptide permease activity" refers to activity of OppA polypeptides described herein. OppA polypeptides are one component of oligopeptide transport systems of the ATP-binding cassette (ABC) family of transporters (Monnet, 2003, Cell. Mol. Life. Sci., 60:2100-2114). Such systems include five parts: an oligopeptide-binding polypeptide which binds substrates, two transmembrane polypeptides, and two polypeptides that hydrolize ATP. An OppA polypeptide described herein binds oligopeptides, typically between two and five amino acids in length, and pass the bound polypeptide to the other components of the oligopeptide transport system for internalization. Methods for determining whether a OppA polypeptide has oligopeptide permease activity are well known to the skilled person.

As used herein, an "isolated" substance is one that has been removed from its natural environment, produced using recombinant techniques, or chemically or enzymatically synthesized. For instance, a polypeptide or a polynucleotide can be isolated. Preferably, a substance is purified, i.e., is at least 60% free, preferably at least 75% free, and most preferably at least 90% free from other components with which they are naturally associated.

As used herein, "identity" refers to sequence similarity between two polypeptides or two polynucleotides. The sequence similarity between two polypeptides is determined by aligning the residues of the two polypeptides (e.g., a candidate amino acid sequence and a reference amino acid sequence, such as SEQ ID NO:2) to optimize the number of identical amino acids along the lengths of their sequences; gaps in either or both sequences are permitted in making the alignment in order to optimize the number of shared amino acids, although the amino acids in each sequence must nonetheless remain in their proper order. The sequence similarity is typically at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity. Sequence similarity may be determined, for example, using sequence techniques such as the BESTFIT algorithm in the GCG package (Madison Wis.), or the Blastp program of the BLAST search algorithm, available through the World Wide Web, for instance at the interne site maintained by the National Center for Biotechnology Information, National Institutes of Health. Preferably, sequence similarity between two amino acid sequences is determined using the Blastp program of the BLAST search algorithm. Preferably, the default values for all Blastp search parameters are used. In the comparison of two amino acid sequences using the BLAST search algorithm, structural similarity is referred to as "identities."

The sequence similarity between two polynucleotides is determined by aligning the residues of the two polynucleotides (e.g., a candidate nucleotide sequence and a reference nucleotide sequence, such as the complement of SEQ ID NO:1) to optimize the number of identical nucleotides along the lengths of their sequences; gaps in either or both sequences are permitted in making the alignment in order to optimize the number of shared nucleotides, although the nucleotides in each sequence must nonetheless remain in their proper order. The sequence similarity is typically at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity. Sequence similarity may be determined, for example, using sequence techniques such as GCG FastA (Genetics Computer Group, Madison, Wis.), MacVector 4.5 (Kodak/IBI software package) or other suitable sequencing programs or methods known in the art. Preferably, sequence similarity between two nucleotide sequences is determined using the Blastn program of the BLAST search algorithm, available through the World Wide Web, for instance at the internet site maintained by the National Center for Biotechnology Information, National Institutes of Health. Preferably, the default values for all Blastn search parameters are used. In the comparison of two nucleotide sequences using the BLAST search algorithm, sequence similarity is referred to as "identities."

Conditions that "allow" an event to occur or conditions that are "suitable" for an event to occur, such as an enzymatic reaction, or "suitable" conditions are conditions that do not prevent such events from occurring. Thus, these conditions permit, enhance, facilitate, and/or are conducive to the event. Such conditions, known in the art and described herein, may depend upon, for example, the antibody being used.

As used herein, a polypeptide "fragment" may retain at least some of the activity of the corresponding native polypeptide. Examples of fragments of polypeptides described herein include, but are not limited to, proteolytic fragments and deletion fragments.

As used herein, "genetically modified microbe" refers to a microbe that has been altered by human intervention. For example, a microbe is a genetically modified microbe by virtue of introduction into a suitable microbe of an exogenous polynucleotide that is foreign to the microbe. "Genetically modified microbe" also refers to a microbe that has been genetically manipulated such that endogenous nucleotides have been altered. For example, a microbe is a genetically modified microbe by virtue of introduction into a suitable microbe of an alteration of endogenous nucleotides. For instance, an endogenous coding region could be deleted or modified to include a mutation. Such mutations may result in a polypeptide having a different amino acid sequence than was encoded by the endogenous polynucleotide, or not being expressed. Another example of a genetically modified microbe is one having an altered regulatory sequence, such as a promoter, to result in increased or decreased expression of an operably linked endogenous coding region.

As used herein, an antibody that can "specifically bind" or is "specific for" a polypeptide is an antibody that interacts only with an epitope of the antigen that induced the synthesis of the antibody, or interacts with a structurally related epitope.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The summary of the present invention presented below is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 11. A. Full length alignment between an OppA polypeptide of the present invention (SEQ ID NO:2, top sequence) and an *Actinobacillus pleuropneumoniae* oligopeptide permease (SEQ ID NO:4, bottom sequence). ":" refers to identity between the two sequences. B. Nucleotide sequence encoding SEQ ID NO:4.

FIG. 12. Full length alignment between an OppA polypeptide of the present invention (SEQ ID NO:2, top sequence), an *Actinobacillus minor* oligopeptide permease (SEQ ID NO:5, second sequence), an *Actinobacillus pleuropneumoniae* oligopeptide permease (SEQ ID NO:4, third sequence), and a *Mannheimia haemolytica* oligopeptide permease (SEQ ID NO:6, fourth sequence). "*" refers to identity between the four sequences.

FIG. 13. Polypeptides expressed by subclones. The polyhistidine is underlined and the protease cleavage sites (ENLYFQG, SEQ ID NO:10, and DDDDK, SEQ ID NO:11) are shaded.

FIG. 14. A nucleotide sequence (SEQ ID NO:9) encoding SEQ ID NO:2.

DETAILED DESCRIPTION OF ILLUSTRATIVE EMBODIMENTS

Figure 1:
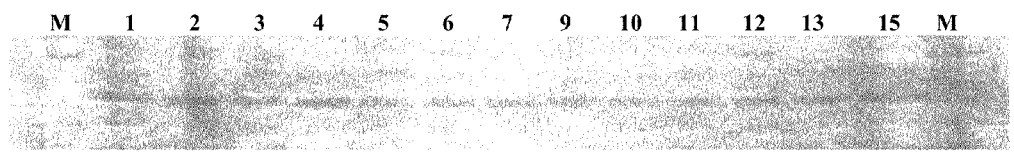
FIG. 1. Detection of the immunogenic species-specific antigen in 13 *Haemophilus parasuis* reference strains by western blot of whole cell protein profiles. Serotypes are indicated above each well; M, molecular weight marker.

The present invention includes isolated polypeptides having oligopeptide permease activity. A polypeptide having oligopeptide permease activity is referred to herein as an OppA polypeptide. An example of an OppA polypeptide is depicted at SEQ ID NO:2. Other examples of OppA polypeptides of the present invention include those having sequence similarity with the amino acid sequence of SEQ ID NO:2. An OppA polypeptide having sequence similarity with the amino acid sequence of SEQ ID NO:2 has oligopeptide permease activity. An OppA polypeptide may be isolated from a microbe, such as a member of the genera Pasteurellaceae, such as a *Haemophilus parasuis*. The *H. parasuis* may be of any serotype, including, but not limited to 1, 2, 3, 4, 5, 6, 7, 8, 9, 10, 11, 12, 13, 14, or 15, or may be non-typable. An OppA polypeptide may be produced using recombinant techniques, or chemically or enzymatically synthesized using routine methods.

The amino acid sequence of an OppA polypeptide having sequence similarity to SEQ ID NO:2 may include conservative substitutions of amino acids present in SEQ ID NO:2. A conservative substitution is typically the substitution of one amino acid for another that is a member of the same class. For example, it is well known in the art of protein biochemistry that an amino acid belonging to a grouping of amino acids having a particular size or characteristic (such as charge, hydrophobicity, and/or hydrophilicity) may generally be substituted for another amino acid without substantially altering the secondary and/or tertiary structure of a polypeptide. Conservative amino acid substitutions can result from exchange of amino acids residues from within one of the following classes of residues: Class I: Gly, Ala, Val, Leu, and Ile (representing aliphatic side chains); Class II: Gly, Ala, Val, Leu, Ile, Ser, and Thr (representing aliphatic and aliphatic hydroxyl side chains); Class III: Tyr, Ser, and Thr (representing hydroxyl side chains); Class IV: Cys and Met (representing sulfur-containing side chains); Class V: Glu, Asp, Asn and Gln (carboxyl or amide group containing side chains); Class VI: His, Arg and Lys (representing basic side chains); Class VII: Gly, Ala, Pro, Trp, Tyr, Ile, Val, Leu, Phe and Met (representing hydrophobic side chains); Class VIII: Phe, Trp, and Tyr (representing aromatic side chains); and Class IX: Asn and Gln (representing amide side chains). The classes are not limited to naturally occurring amino acids, but also include artificial amino acids, such as beta or gamma amino acids and those containing non-natural side chains, and/or other similar monomers such as hydroxyacids. SEQ ID NO:2 is shown in FIG. 12 in a multiple protein alignment with three other proteins having oligopeptide permease activity. Identical amino acids between all four are marked with a "*." Significant domains of conserved amino acids are present, and the skilled person could predict which amino acids of SEQ ID NO:2 could be varied without losing activity. The structural basis for peptide binding by OppA polypeptides is also known (Tame et al., 1994, Science, 264:1578-1581, and Tame et al., 1995, Structure, 3:1395-1406).

Guidance concerning how to make phenotypically silent amino acid substitutions is provided in Bowie et al. (1990, Science, 247:1306-1310), wherein the authors indicate proteins are surprisingly tolerant of amino acid substitutions. For example, Bowie et al. disclose that there are two main approaches for studying the tolerance of a polypeptide sequence to change. The first method relies on the process of evolution, in which mutations are either accepted or rejected by natural selection. The second approach uses genetic engineering to introduce amino acid changes at specific positions of a cloned gene and selects or screens to identify sequences that maintain functionality. As stated by the authors, these studies have revealed that proteins are surprisingly tolerant of amino acid substitutions. The authors further indicate which changes are likely to be permissive at a certain position of the protein. For example, most buried amino acid residues require non-polar side chains, whereas few features of surface side chains are generally conserved. Other such phenotypically silent substitutions are described in Bowie et al, and the references cited therein.

The present invention also includes isolated polynucleotides encoding a polypeptide of the present invention. A polynucleotide encoding an OppA polypeptide is referred to herein as an oppA polynucleotide. oppA polynucleotides may have a nucleotide sequence encoding a polypeptide having the amino acid sequence shown in SEQ ID NO:2. An example of the class of nucleotide sequences encoding such a polypeptide is the complement of SEQ ID NO:1, preferably the reverse complement of nucleotides 1-1,542 of SEQ ID NO: 1. It should be understood that a polynucleotide encoding a OppA polypeptide represented by SEQ ID NO:2 is not limited to the nucleotide sequence disclosed at the complement of SEQ ID NO:1, but also includes the class of polynucleotides encoding such polypeptides as a result of the degeneracy of the genetic code. For example, the naturally occurring complement of SEQ ID NO:1 is but one member of the class of nucleotide sequences encoding a polypeptide having the amino acid sequence SEQ ID NO:2. The class of nucleotide sequences encoding a selected polypeptide sequence is large but finite, and the nucleotide sequence of each member of the class may be readily determined by one skilled in the art by reference to the standard genetic code, wherein different nucleotide triplets (codons) are known to encode the same amino acid.

An oppA polynucleotide of the present invention may have sequence similarity with the nucleotide sequence of SEQ ID NO:1, preferably the reverse complement of nucleotides 1-1,542 of SEQ ID NO:1. oppA polynucleotides having sequence similarity with the nucleotide sequence of SEQ ID NO:1 encode an OppA polypeptide. An oppA polynucleotide may be isolated from a microbe, such as a member of the genera *Pasteurellaceae*, such as an *H. parasuis*, or may be produced using recombinant techniques, or chemically or enzymatically synthesized. An oppA polynucleotide of the present invention may further include heterologous nucleotides flanking the open reading frame encoding the oppA polynucleotide. Typically, heterologous nucleotides may be at the 5' end of the coding region, at the 3' end of the coding region, or the combination thereof. The number of heterologous nucleotides may be, for instance, at least 10, at least 100, or at least 1000.

Whether a polypeptide has oligopeptide permease activity may be determined by in vitro assays. Such assays are known to the person skilled in the art and are routine.

The present invention also includes fragments of the polypeptides described herein, and the polynucleotides encoding such fragments. A fragment may include antigenic epitopes that are not present on the oligopeptide permease expressed by *Actinobacillus pleuropneumoniae* and described at Genbank accession number ABY69417.1 (SEQ ID NO:4, which is encoded by nucleotides 948758-950332 of Genbank accession number CP000687, SEQ ID NO:3, FIG. 11). A polypeptide fragment may include a sequence of at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, or at least 100 amino acid residues.

A polypeptide of the present invention or a fragment thereof may be expressed as a fusion polypeptide that includes a polypeptide of the present invention or a fragment thereof and an additional amino acid sequence. For instance, the additional amino acid sequence may be useful for purification of the fusion polypeptide by affinity chromatography. Various methods are available for the addition of such affinity purification moieties to proteins. Representative examples include, for instance, a polyhistidine-tag (His-tag) and maltose-binding protein (see, for instance, Hopp et al. (U.S. Pat. No. 4,703,004), Hopp et al. (U.S. Pat. No. 4,782,137), Sgarlato (U.S. Pat. No. 5,935,824), and Sharma (U.S. Pat. No. 5,594,115)). In another example, the additional amino acid sequence may be a carrier polypeptide. The carrier polypeptide may be used to increase the immunogenicity of the fusion polypeptide to increase production of antibodies that specifically bind to a polypeptide of the invention. The invention is not limited by the types of carrier polypeptides that may be used to create fusion polypeptides. Examples of carrier polypeptides include, but are not limited to, keyhole limpet hemacyanin, bovine serum albumin, ovalbumin, mouse serum albumin, rabbit serum albumin, and the like.

A polynucleotide of the present invention may be present in a vector. A vector is a replicating polynucleotide, such as a plasmid, phage, or cosmid, to which another polynucleotide may be attached so as to bring about the replication of the attached polynucleotide. Construction of vectors containing a polynucleotide of the invention employs standard ligation techniques known in the art. See, e.g., Sambrook et al, Molecular Cloning: A Laboratory Manual, Cold Spring Harbor Laboratory Press (1989). A vector may provide for further cloning (amplification of the polynucleotide), i.e., a cloning vector, or for expression of the polynucleotide, i.e., an expression vector. The term vector includes, but is not limited to, plasmid vectors, viral vectors, cosmid vectors, and artificial chromosome vectors. Examples of viral vectors include, for instance, lambda phage vectors, P1 phage vectors, M13 phage vectors, adenoviral vectors, adeno-associated viral vectors, lentiviral vectors, retroviral vectors, and herpes virus vectors. Typically, a vector is capable of replication in a microbial host, for instance, a prokaryotic bacterium, such as *E. coli*. Preferably the vector is a plasmid.

Selection of a vector depends upon a variety of desired characteristics in the resulting construct, such as a selection marker, vector replication rate, and the like. In some aspects, suitable host cells for cloning or expressing the vectors herein include prokaryotic cells. Suitable prokaryotic cells include eubacteria, such as gram-negative microbes, for example, *E. coli*. Vectors may be introduced into a host cell using methods that are known and used routinely by the skilled person. For example, calcium phosphate precipitation, electroporation, heat shock, lipofection, microinjection, and viral-mediated nucleic acid transfer are common methods for introducing nucleic acids into host cells.

Polynucleotides of the present invention may be obtained from microbes, for instance, *H. parasuis*. *H. parasuis* useful in the present invention may be obtained from pigs, preferably pigs showing signs and/or symptoms of *H. parasuis* disease. Accordingly, in some embodiments a useful *H. parasuis* is one capable of causing disease in a pig. Polynucleotides of the present invention may be produced in vitro or in vivo. For instance, methods for in vitro synthesis include, but are not limited to, chemical synthesis with a conventional DNA/RNA synthesizer. Commercial suppliers of synthetic polynucleotides and reagents for such synthesis are well known. Likewise, polypeptides of the present invention may be obtained from microbes, or produced in vitro or in vivo.

An expression vector optionally includes regulatory sequences operably linked to the coding region. The invention is not limited by the use of any particular promoter, and a wide variety of promoters are known. Promoters act as regulatory signals that bind RNA polymerase in a cell to initiate transcription of a downstream (3' direction) coding region. The promoter used may be a constitutive or an inducible promoter. It may be, but need not be, heterologous with respect to the host cell.

An expression vector may optionally include a ribosome binding site and a start site (e.g., the codon ATG or GTG) to initiate translation of the transcribed message to produce the polypeptide. It may also include a termination sequence to end translation. A termination sequence is typically a codon for which there exists no corresponding aminoacetyl-tRNA, thus ending polypeptide synthesis. The polynucleotide used to transform the host cell may optionally further include a transcription termination sequence.

A vector introduced into a host cell optionally includes one or more marker sequences, which typically encode a molecule that inactivates or otherwise detects or is detected by a compound in the growth medium. For example, the inclusion of a marker sequence may render the transformed cell resistant to an antibiotic, or it may confer compound-specific metabolism on the transformed cell. Examples of a marker sequence are sequences that confer resistance to kanamycin, ampicillin, chloramphenicol, tetracycline, and neomycin.

The present invention also includes antibodies that specifically bind a polypeptide of the present invention. An antibody that specifically binds an OppA polypeptide of the present invention, preferably, SEQ ID NO:2 or a fragment thereof, does not bind to an oligopeptide permease expressed by *Actinobacillus pleuropneumoniae* and described at Genbank accession number ABY69417.1 (SEQ ID NO:4).

Antibody may be produced using a polypeptide of the present invention, or a fragment thereof. The antibody may be polyclonal or monoclonal. Laboratory methods for producing, characterizing, and optionally isolating polyclonal and monoclonal antibodies are known in the art (see, for instance, Harlow E. et al., 1988, Antibodies: A laboratory manual, Cold Spring Harbor Laboratory Press, Cold Spring Harbor). For instance, a polypeptide of the present invention may be administered to an animal, such as a mammal or a chicken, in an amount effective to cause the production of antibody specific for the administered polypeptide. Optionally, a polypeptide may be mixed with an adjuvant, for instance Freund's incomplete adjuvant, to stimulate the production of antibodies upon administration. Production of antibody that specifically binds SEQ ID NO:2 and does not specifically bind SEQ ID NO:4 may be accomplished by use of one or more fragments from SEQ ID NO:2 that have reduced identity with a series of amino acids in SEQ ID NO:4. By way of example and without intending to be limiting, fragments of SEQ ID NO:2 that include, for instance, amino acids 30 to 47, 361 to 382, or 397 to 412 (see FIG. 11), may be administered to an animal. The antibodies that result would be expected to include those specifically binding to SEQ ID NO:2 and not specifically binding to SEQ ID NO:4.

An antibody of the present invention may be produced by recombinant methods known in the art. An antibody of the present invention may be modified by recombinant means to increase efficacy of the antibody in mediating the desired function.

Antibody fragments include at least a portion of the variable region of an antibody that specifically binds to its target. Examples of antibody fragments include, for instance, scFv, Fab, $F(ab')_2$, Fv, a single chain variable region, and the like. Fragments of intact molecules can be generated using methods well known in the art and include enzymatic digestion and recombinant means.

Whether an antibody of the present invention specifically binds to a polypeptide of the present invention may be determined using methods known in the art. For instance, specificity may be determined by testing antibody binding to SEQ ID NO:2 and a polypeptide having the amino acid sequence described at Genbank accession number ABY69417.1 (SEQ ID NO:4).

An antibody of the present invention may be coupled (also referred to as conjugated) to a detectable label, e.g., a molecule that is easily detected by various methods. Examples include, but are not limited to, radioactive elements; enzymes (such as horseradish peroxidase, alkaline phosphatase, and the like); fluorescent, phosphorescent, and chemiluminescent dyes; latex and magnetic particles; cofactors (such as biotin); dye crystallites, gold, silver, and selenium colloidal particles; metal chelates; coenzymes; electroactive groups; oligonucleotides, stable radicals, and others. Methods for conjugating a detectable label to antibody vary with the type of label, and such methods are known and routinely used by the person skilled in the art.

Also provided herein are other molecules that specifically bind a polypeptide of the present invention. Examples of such molecules include DNA and/or RNA aptamers. Methods for making such molecules are known to the skilled person and are routine.

The present invention also includes genetically modified microbes and compositions that include genetically modified microbes. In some embodiments a genetically modified microbe has an exogenous polynucleotide encoding an OppA polypeptide described herein, or a fragment thereof. Compared to a control microbe that is not genetically modified, a genetically modified microbe may exhibit production of an OppA polypeptide or a fragment thereof. A polynucleotide encoding an OppA polypeptide may be present in the microbe as a vector or integrated into a chromosome. Examples of microbes that can be genetically modified to include an exogenous polynucleotide encoding an OppA polypeptide described herein, or a fragment thereof, include, but are not limited to, attenuated microbes such as Bacille Calmette-Guerin (BCG), *Listeria monocytogenes*, *Salmonellae*, *Shigellae*, and *E. coli*.

In another aspect, a genetically modified microbe is an *H. parasuis*. The *H. parasuis* may include a polynucleotide encoding an OppA polypeptide (an oppA coding region), where the oppA coding region includes a mutation. The mutation may be one that results in attenuation of the microbe. An attenuated microbe is able to replicate in an animal and induce an immune response, but generally is not pathogenic and has a reduced ability to cause the clinical signs and/or symptoms of disease in an animal. An attenuated *H. parasuis* has a reduced ability to cause in pigs the clinical signs of pneumonia, arthritis, meningitis, pleuritis, and peritonitis. Whether a genetically modified *H. parasuis* is attenuated can be determined by testing using pigs, the natural host for *H. parasuis*, or guinea pigs, a model system recognized in the art as relevant in the study of *H. parasuis* pathogenesis in pigs.

Examples of mutations that can be used in the production of a genetically modified *H. parasuis* include point mutations, such as transition and/or transversion point mutations, deletions, and insertions. A deletion may include deletion of part or an entire nucleotide sequence encoding OppA, or deletion of a regulatory region of an oppA coding region. The genetically modified *H. parasuis* may encode a fragment of an OppA polypeptide or not encode an OppA polypeptide. If the genetically modified *H. parasuis* encodes a fragment of an OppA polypeptide, the polypeptide typically does not have oligopeptide permease activity. Typically, a mutation useful to produce a genetically modified *H. parasuis* for use in one of the methods described herein is stable and non-reverting.

A variety of methods that can be used to modify an oppA coding region in an *H. parausis* are known and used routinely by the skilled person. For instance, DNA integration cassettes (also referred to as DNA mutagenic cassettes) can be used to replace a chromosomal oppA coding region in a wild-type cell by homologous recombination. Such cassettes typically include the mutation to be inserted, homologous nucleotide sequences to target the mutation to the oppA coding region, and a marker sequence. The actual nucleotide sequence of an oppA coding region in an *H. parasuis* may vary slightly from a publicly available sequence; however, the actual nucleotide sequence can be easily determined using routine methods to clone the coding region and determine the nucleotide sequence. Typically, the cloning of the coding region can be accomplished by use of the known nucleotide sequence in many routine techniques including, for instance, making primers for use in a polymerase chain reaction to amplify the coding region, or making a probe to screen a library for the coding region.

The present invention also provides compositions including a genetically modified microbe, polypeptides, polynucleotides, molecules that specifically bind an OppA polypeptide described herein (such as an antibody), or combinations thereof. Such compositions may include a pharmaceutically acceptable carrier. As used herein "pharmaceutically acceptable carrier" includes saline, solvents, dispersion media, coatings, antibacterial and antifungal agents, isotonic and absorption delaying agents, and the like, compatible with pharmaceutical administration and not deleterious to a recipient thereof. A composition of the present invention may be referred to as a vaccine. The term "vaccine" as used herein refers to a composition that, upon administration to an animal, will increase the likelihood the recipient is protected against *H. parasuis*. For instance, when the composition includes or encodes an immunogenic polypeptide, administration to the animal typically produces an immunological response to the polypeptide and results in immunity.

The compositions of the present invention may be formulated in pharmaceutical preparations in a variety of forms adapted to the chosen route of administration, including routes suitable for stimulating an immune response to an antigen. Thus, a composition of the present invention can be administered via known routes including, for example, oral; parenteral including intradermal, transcutaneous and subcutaneous; intramuscular, intravenous, intraperitoneal, etc. and topically, such as, intranasal, intrapulmonary, intramammary, intravaginal, intrauterine, intradermal, transcutaneous and rectally, etc. It is foreseen that a composition can be administered to a mucosal surface, such as by administration to the nasal or respiratory mucosa (e.g., via a spray or aerosol), in order to stimulate mucosal immunity, such as production of secretory IgA antibodies, throughout the animal's body.

A composition may include a polypeptide described herein. Such a composition is often referred to as a subunit vaccine. The polypeptides present in the composition may be obtained by isolation or purification from an *H. parasuis*, or by using recombinant, enzymatic, or chemical techniques described herein, such as expression systems (e.g., expression in an *E. coli* host) followed by isolation or purification of the polypeptide.

A composition may include a polynucleotide of the present invention. The polynucleotide can include DNA, RNA, or a combination thereof. The polynucleotide may be supplied as part of a vector or as a "naked" polynucleotide.

The formulations may be conveniently presented in unit dosage form and may be prepared by methods well known in the art of pharmacy. Methods of preparing a composition with a pharmaceutically acceptable carrier include the step of bringing the active compound (e.g., a polypeptide or genetically modified microbe) into association with a carrier that constitutes one or more accessory ingredients. In general, the formulations are prepared by uniformly and intimately bringing the active compound into association with a liquid carrier, a finely divided solid carrier, or both, and then, if necessary, shaping the product into the desired formulations. In general, a composition can be formulated to be compatible with its intended route of administration. More specifically, the compositions of the present invention may be administered to any tissue of an animal, including, but not limited to, muscle (such as skeletal muscle or cardiac muscle), skin, lung tissue, intestinal tissue, and the like. A composition of the present invention may be administered to any internal cavity of an animal, including, but not limited to, lungs, mouth, nasal cavity, stomach, peritoneal cavity, intestine, veins, and the like.

A composition including a pharmaceutically acceptable carrier can also include an adjuvant. An "adjuvant" refers to an agent that can act in a nonspecific manner to enhance an immune response to a particular antigen, thus potentially reducing the quantity of antigen necessary in any given immunizing composition, and/or the frequency of injection necessary in order to generate an adequate immune response to the antigen of interest. Adjuvants may include, for example, IL-1, IL-2, emulsifiers, muramyl dipeptides, dimethyl dioctadecyl ammonium bromide (DDA), pyridine, aluminum hydroxide, oils, saponins, alpha-tocopherol, polysaccharides, emulsified paraffins, ISA-70, RIBI and other substances known in the art.

In another embodiment, a composition of the invention including a pharmaceutically acceptable carrier can include a biological response modifier, such as, for example, IL-2, IL-4 and/or IL-6, TNF, IFN-alpha, IFN-gamma, and other cytokines that effect immune cells. An immunizing composition can also include other components known in the art such as antibiotics, preservatives, anti-oxidants, or chelating agents.

Any route of administration may be used so long as it results in the delivery of an amount sufficient to generate an immune response (e.g., when polypeptide, polynucleotide, or attenuated *H. parasuis* is administered) or a protective response (e.g., when an antibody is administered) in an animal in need of such response.

A composition of the present invention may be administered in an amount sufficient to treat certain conditions as described herein. For instance, the amount of polypeptides or genetically modified microbe present in a composition of the present invention can vary. For example, the dosage of polypeptides can be between 0.01 micrograms (μg) and 300 milligrams (mg), typically between 0.05 mg and 10 mg. When the composition is a preparation including genetically modified microbes, the cells can be present at a concentration of, for instance, at least $10^2$ bacteria/ml, at least $10^3$ bacteria/ml, at least $10^4$ bacteria/ml, at least $10^5$ bacteria/ml, at least $10^6$ bacteria/ml, at least $10^7$ bacteria/ml, at least $10^8$ bacteria/ml, or at least $10^9$ bacteria/ml. For an injectable composition (e.g. subcutaneous, intramuscular, etc.) the polypeptides may be present in the composition in an amount such that the total volume of the composition administered is 0.5 ml to 5.0 ml, typically 1.0 to 2.0 ml. When the composition is a preparation of genetically modified microbes, the cells are preferably present in the composition in an amount that the total volume of the composition administered is 0.5 ml to 5.0 ml, typically 1.0 to 2.0 ml. The amount administered will vary depending on various factors including, but not limited to, the specific polypeptides chosen, the weight, physical condition and age of the animal, and the route of administration. Thus, the absolute weight of the polypeptide included in a given unit dosage form can vary widely, and depends upon factors such as the species, age, weight and physical condition of the animal, as well as the method of administration. Such factors can be determined by one of skill in the art.

The present invention is also directed to methods of using the compositions described herein. In one aspect, the present invention provides methods for detecting antibody that specifically binds an OppA polypeptide described herein. These methods are useful in, for instance, detecting whether an animal has antibody that specifically binds polypeptides of the present invention, diagnosing whether an animal has been systemically infected by *H. parasuis*, or monitoring maternal antibody levels to predict when a vaccine may be given to a young animal. Such diagnostic systems may be in kit form. The methods typically include testing a biological sample obtained from an animal for the presence of antibody that specifically binds an OppA polypeptide described herein. The biological sample may be derived from the circulatory system and may be, for instance, blood (including serum), oral fluid (such as saliva), colostrum, or nasal, tracheal, bronchial, or lung lavage. The method may include contacting an antibody with a preparation that includes an OppA polypeptide described herein to result in a mixture. The method may further includes incubating the mixture under conditions to allow the antibody to specifically bind the polypeptide to a polypeptide:antibody complex. As used herein, the term "polypeptide:antibody complex" refers to the complex that results when an antibody specifically binds to a polypeptide. The preparation that includes the polypeptides of the present invention may also include reagents, for instance a buffer, that provide conditions appropriate for the formation of the polypeptide:antibody complex. The polypeptide:antibody complex is then detected.

These assays may be performed within various immunological assay formats known in the art and routinely used, including but not limited to various types of radioimmunoassays, enzyme-linked immunosorbent assays (ELISA), enzyme-linked immunofluorescent assays (ELIFA), immunoprecipitation, Western blot analysis, serum neutralization, such as standard SN and modified SN, and the like. The OppA polypeptide may be in solution or bound to a surface, such as polystyrene or microsphere. In one embodiment, an OppA polypeptide described herein may be bound to the surface of a well, and a biological sample added to the well and incubated under conditions suitable for the formation of a polypeptide:antibody complex between the bound OppA polypeptide and any anti-OppA antibody present in the biological sample. Detection of the anti-OppA antibody may be accomplished using various routine detection methods known in the art, including, for instance, antibodies that will specifically bind the polypeptide:antibody complex. Such antibodies, including anti-pig antibody, are commercially available and can be easily made. Such antibodies may be conjugated to a detectable label, such as radioactive elements; enzymes (such as horseradish peroxidase and alkaline phosphatase); fluorescent, phosphorescent, and chemiluminescent dyes; latex and magnetic particles; cofactors (such as biotin); dye crystallites, gold, silver, and selenium colloidal particles; metal chelates; coenzymes; electroactive groups; oligonucleotides, stable radicals, and others.

In one embodiment, the methods may be used to monitor maternal antibody levels to predict when a vaccine may be given to a newborn animal. Newborn animals typically have no antibodies of their own, and are not capable of producing antibody until their immune system has matured. A newborn animal obtains antibody helpful in protection from pathogens by ingesting its mother's milk (maternal colostrum) soon after birth; however, this antibody can neutralize vaccine antigens preventing stimulation of the immune system. Thus, it can be useful to know the level of maternal antibody to an antigen present before administration of that antigen. In some embodiments, the titer of maternal antibody to an OppA polypeptide described herein can be determined as described herein. Once the maternal antibody titer is known, it is possible to predict when the maternal antibody titer will drop to a level that permits vaccination with, for instance, an OppA polypeptide.

Other methods of using the compositions described herein include, for instance, methods for detecting an OppA polypeptide. These methods are useful in, but not limited to, detecting *H. parasuis* in an animal, detecting *H. parasuis* in tissues from an animal, and diagnosing a disease caused by *H. parasuis* (including during an infection or after an infection). Such diagnostic systems may be in kit form. The methods typically include testing a biological sample obtained from an animal for the presence of an OppA polypeptide described herein. The biological sample may be derived from the circulatory system and may be, for instance, blood (including serum), oral fluid (such as saliva), colostrum, or nasal, tracheal, bronchial, or lung lavage. The biological sample may be derived from the lymphatic system and may be, for instance, tonsil tissue. The method may include contacting an OppA polypeptide described herein with a preparation that includes an antibody to result in a mixture. The method may further include incubating the mixture under conditions to allow the antibody to specifically bind the polypeptide to form a polypeptide:antibody complex. The preparation that includes the antibody may also include reagents, for instance a buffer, that provide conditions appropriate for the formation of the polypeptide:antibody complex. The polypeptide:antibody complex is then detected.

These assays may be performed within various immunological assay formats known in the art and routinely used, including but not limited to various types of radioimmunoassays, enzyme-linked immunosorbent assays (ELISA), enzyme-linked immunofluorescent assays (ELIFA), immunocytochemical methods, immunoprecipitation, immunohistochemical analysis, Western blot analysis, serum neutralization, such as standard SN and modified SN, and the like. The antibody may be in solution or bound to a surface, such as polystyrene or microsphere. In one embodiment, an antibody that specifically binds an OppA polypeptide described herein may be bound to the surface of a well, and a biological sample added to the well and incubated under conditions suitable for the formation of a polypeptide:antibody complex between the anti-OppA antibody OppA polypeptide present in the biological sample. Detection of the polypeptide:antibody complex may be accomplished using various detection methods known in the art and used routinely, including, for instance, antibodies that will specifically bind the polypeptide:antibody complex, such as anti-OppA antibody. Such antibodies can be easily made. Such antibodies may be conjugated to a detectable label, such as radioactive elements; enzymes (such as horseradish peroxidase and alkaline phosphatase); fluorescent, phosphorescent, and chemiluminescent dyes; latex and magnetic particles; cofactors (such as biotin); dye crystallites, gold, silver, and selenium colloidal particles; metal chelates; coenzymes; electroactive groups; oligonucleotides, stable radicals, and others.

In some aspects of the invention, detecting *H. parasuis* includes detecting such a microbe in an animal. These methods may include providing a biological sample from an animal. In this aspect the animal is one that is suspected of harboring the microbe (presently infected), or may be a member of a group that is being screened for the presence of *H. parasuis*. Antibody the specifically binds OppA described herein may be mixed with the biological sample and incubated under conditions to form a complex with *H. parasuis*. The complex is then detected, and the presence of the complex indicates the presence of *H. parasuis* in the biological sample. The complex may be antibody:*H. parasuis*, or antibody:OppA polypeptide. The detection of antibodies is known in the art and may include, for instance, immunofluorescence and peroxidase.

Other methods for detecting a *H. parasuis* include the amplification of an oppA polynucleotide, such as by the polymerase chain reaction (PCR), microarrays, hybridization using probes, such as in situ hybridization, and the like. The polynucleotide may be one that is, for instance, present in a biological sample from an animal that is suspected of harboring the *H. parasuis*, or a member of a group that is being screened for the presence of the *H. parasuis*.

The method may include contacting a biological sample that may include an oppA polynucleotide with an oligonucleotide, such as a probe for hybridization, or a primer pair for amplification. Amplification includes incubation under conditions to form a detectable amplified polynucleotide. As used herein, a "primer pair" refers to two single stranded polynucleotides that can be used together to amplify a region of a polynucleotide, preferably by a PCR. Many variations of PCR exist, including, for instance, real time PCR and mass tag PCR, and are useful herein. The polynucleotide that results from amplifying a region of a polynucleotide is referred to as an "amplification product" or an "amplified polynucleotide."

Primers that amplify a portion of an oppA polynucleotide can be designed using readily available computer programs, such as DNAStar Lasergene (Madison, Wis.) and Primer3 (Rozen and Skaletsky, 2000, In: Krawetz and Misener (eds.), Bioinformatics Methods and Protocols: Methods in Molecular Biology. Humana Press, Totowa, N.J., pp 365-386). Factors that can be considered in designing primers include, but are not limited to, melting temperatures, primer length, size of the amplification product, and specificity. Primer length is generally between about 15 and about 30 nucleotides. The conditions for amplifying a polynucleotide by PCR vary depending on the nucleotide sequence of primers used, and methods for determining such conditions are routine in the art. An example of a primer pair that can be used to amplify an oppA coding region from *H. parasuis* and not amplify an oppA coding region from another microbe is 5'-CGGCTTA-CACCAATGAATGA (forward) (SEQ ID NO:7) and 5'-GT-GTTGGTGCTGGTTTAGCA (reverse) (SEQ ID NO:8). The size of the amplified polynucleotide is 1,519 bases.

Typical formats in which polynucleotides, such as primer pairs and/or probes, may be used to detect *H. parasuis* include the use of polynucleotides in solution or bound to a surface, such as polystyrene or microsphere.

The methods further include methods for genotyping an *H. parasuis* isolated from a pig or detected in clinical samples by PCR. The genomic region analyzed when genotyping an *H. parasuis* includes nucleotides present in an oppA coding region. Typically, a portion of an oppA coding region is amplified and then either the nucleotide sequence of the amplified fragment is determined, or the amplified fragment is subjected to restriction fragment length polymorphism (RFLP) analysis. The sequence of the amplified fragment or the restriction fragments may be compared for strain identification based on oppA sequence type. Preferably, when the nucleotide sequence of an amplified fragment is determined, nucleotides near the 3' end are used for strain typing (nucleotides 667-1394). For instance, when the primers described above are used for amplification of the oppA gene, the reverse primer may be used as the primer for sequencing. Thus, an oppA coding region described herein may be used as a molecular epidemiology marker for strain differentiation. Moreover, the identification of *H. parasuis* strains based on oppA sequencing permits quick selection of strains that can be used in the production of an autogenous vaccine.

Methods for using the compositions described herein also include administering to an animal an effective amount of a composition of the present invention, for instance an OppA polypeptide or fragment thereof, or a genetically modified microbe. The animal can be, for instance, porcine (including, for instance, swine), avian (including, for instance, chickens or turkeys), bovine (including, for instance, cattle and bison), caprine (including, for instance, goats), ovine (including, for instance, sheep), equine (including, for instance, horses), a companion animal (including, for instance, dogs or cats), members of the family Cervidae (including, for instance, deer, elk, moose, caribou and reindeer), murine (including, for instance, mice or rats), or human.

In some aspects, the methods may further include additional administrations (e.g., one or more booster administrations) of the composition to the animal to enhance or stimulate a secondary immune response. A booster can be administered at a time after the first administration, for instance, one to eight weeks, preferably two to four weeks, after the first administration of the composition. Subsequent boosters can be administered one, two, three, four, or more times annually.

In one aspect the invention is directed to treating an infection in an animal, caused by an *H. parasuis*. As used herein, the term "infection" refers to the presence of an *H. parasuis* in an animal's body and interfering with the normal functioning of the host animal.

Treating an infection can be prophylactic or, alternatively, can be initiated after the animal is infected by the microbe. Treatment that is prophylactic—e.g., initiated before a subject is infected by a microbe or while any infection remains subclinical—is referred to herein as treatment of a subject that is "at risk" of infection. As used herein, the term "at risk" refers to an animal that may or may not actually possess the described risk. Thus, typically, an animal "at risk" of infection by a microbe is an animal present in an area where animals have been identified as infected by the microbe and/or is likely to be exposed to the microbe even if the animal has not yet manifested any detectable indication of infection by the microbe and regardless of whether the animal may harbor a subclinical amount of the microbe. Accordingly, administration of a composition can be performed before, during, or after the animal has first contact with the microbe. Treatment initiated after the animal's first contact with the microbe may result in decreasing the severity of symptoms and/or clinical signs of infection by the microbe, completely removing the microbe, and/or decreasing the likelihood of experiencing a clinically evident infection compared to an animal to which the composition is not administered.

The method includes administering an effective amount of the composition of the present invention to an animal having, or at risk of having, an infection caused by an *H. parasuis*, and optionally determining whether the number of microbes causing the infection has decreased. In this aspect of the invention, an "effective amount" is an amount effective to reduce the number of the specified microbes in an animal or reduce the likelihood that the animal experiences a clinically-evident infection compared to an animal to which the composition is not administered. Methods for determining whether an infection is caused by an *H. parasuis* are routine and known in the art, as are methods for determining whether the infection has decreased. Such methods include, for instance, measuring tissues colonized by *H. parasuis* during infection for the presence and/or absence and/or quantity of *H. parasuis*.

In another embodiment, the method includes administering an effective amount of the composition of the present invention to an animal having, or at risk of having, an infection caused by an *H. parasuis*, and optionally determining whether an immune response against the antigen, for instance, the OppA polypeptide or the genetically modified microbe, has occurred in the animal. In this aspect of the invention, an "effective amount" is an amount effective to result in an immune response to the administered antigen. Without intending to be limiting, this aspect of the invention may be useful to induce an immune response in a breeding female, such as a sow. An immune response in a sow against the administered antigen can be passed to the sow's offspring via maternal colostrum, resulting in the passive transfer of immunity. This is particularly advantageous with farm animals, as passive transfer of immunity generally does not occur through the placenta before birth.

In another aspect, the present invention is directed to methods for treating one or more symptoms or clinical signs of certain conditions in an animal that may be caused by infection by an *H. parasuis*. The method includes administering an effective amount of a composition of the present invention to an animal having or at risk of having a condition, or exhibiting symptoms and/or clinical signs of a condition, and determining whether at least one symptom and/or clinical sign of the condition is changed, preferably, reduced. Examples of conditions and/or clinical signs caused by *H. parasuis* include, but are not limited to, pneumonia, arthritis, meningitis, pleuritis, peritonitis, heart sac infection, fever, respiratory distress, lameness, CNS signs (e.g., lateral decumbency, paddling, and nistagmus), lameness/stiffness, slight swellings over the joints and tendons, and/or a short cough of 2-3 episodes. In swine disease caused by *H. parasuis* is often referred to as Glässers Disease.

Treatment of symptoms and/or clinical signs associated with these conditions can be prophylactic or, alternatively, can be initiated after the development of a condition described herein. As used herein, the term "symptom" refers to subjective evidence of disease or condition experienced by the patient and caused by infection by a microbe. As used herein, the term "clinical sign" or, simply, "sign" refers to objective evidence of disease or condition caused by infection by a microbe. Symptoms and/or clinical signs associated with conditions referred to herein and the evaluations of such symptoms are routine and known in the art. Treatment that is prophylactic, for instance, initiated before a subject manifests symptoms or signs of a condition caused by a microbe, is referred to herein as treatment of a subject that is "at risk" of developing the condition. Thus, typically, an animal "at risk" of developing a condition is an animal present in an area where animals having the condition have been diagnosed and/or is likely to be exposed to a microbe causing the condition even if the animal has not yet manifested symptoms or signs of any condition caused by the microbe. Accordingly, administration of a composition can be performed before, during; or after the occurrence of the conditions described herein. Treatment initiated after the development of a condition may result in decreasing the severity of the symptoms of one of the conditions, or completely removing the symptoms. In this aspect of the invention, an "effective amount" is an amount effective to prevent the manifestation of symptoms of a disease, decrease the severity of the symptoms of a disease, and/or completely remove the symptoms.

The present invention also provides methods for decreasing colonization by an *H. parasuis*, for instance blocking the attachment sites of an *H. parasuis*, including tissues of the skeletal system (for instance, bones, cartilage, tendons and ligaments), muscular system, (for instance, skeletal and smooth muscles), circulatory system (for instance, heart, blood vessels, capillaries and blood), nervous system (for instance, brain, spinal cord, and peripheral nerves), respiratory system (for instance, nasal cavitytrachea lungs, bronchi, bronchioceles, alveoli), digestive system (for instance, mouth, salivary glands oesophagus liver stomach large and small intestine), excretory system (for instance, kidneys, ureters, bladder and urethra), endocrine system (for instance, hypothalamus, pituitary, thyroid, pancreas and adrenal glands), reproductive system (for instance, ovaries, oviduct, uterus, vagina, mammary glands, testes, and seminal vesicles), lymphatic/immune systems (for instance, lymph, lymph nodes and vessels, tonsils, mononuclear or white blood cells, such as macrophages, neutrophils, monocytes, eosinophils, basophils, and lymphocytes, including T cells and B cells), and specific cell lineages (for instance, precursor cells, epithelial cells, stem cells), and the like. As used herein, "colonization" refers to the presence of an *H. parasuis* in an animal's body that is not interfering with the normal functioning of the host animal.

Decreasing colonization in an animal may be performed prophylactically or, alternatively, can be initiated after the animal is colonized by the microbe. Treatment that is prophylactic, e.g., initiated before a subject is colonized by a microbe or while any colonization remains undetected—is referred to herein as treatment of a subject that is "at risk" of colonization by the microbe. Thus, typically, an animal "at risk" of colonization by a microbe is an animal present in an area where animals have been identified as colonized by the microbe and/or is likely to be exposed to the microbe even if the animal has not yet manifested any detectable indication of colonization by the microbe. Accordingly, administration of a composition can be performed before, during, or after the animal has first contact with the microbe. Treatment initiated after the animal's first contact with the microbe may result in decreasing the extent of colonization by the microbe, completely removing the microbe, and/or decreasing the likelihood that the animal becomes colonized by the microbe compared to an animal to which the composition is not administered. Thus, the method includes administering an effective amount of a composition of the present invention to an animal colonized by, or at risk of being colonized by, an *H. parasuis*. In this aspect of the invention, an "effective amount" is an amount sufficient to decrease colonization of the animal by the microbe, where decreasing colonization refers to one or more of: decreasing the extent of colonization by the microbe, completely removing the microbe, and/or decreasing the likelihood that the animal becomes colonized by the microbe compared to an animal to which the composition is not administered. Methods for evaluating the colonization of an animal by a microbe are routine and known in the art.

A composition of the invention can be used to provide for active or passive immunization against bacterial infection. Generally, the composition can be administered to an animal to provide active immunization. However, the composition can also be used to induce production of immune products, such as antibodies, which can be collected from the producing animal and administered to another animal to provide passive immunity. Immune components, such as antibodies, can be collected to prepare compositions (preferably containing antibody) from serum, plasma, blood, colostrum, etc. for passive immunization therapies. Passive antibody compositions and fragments thereof, e.g., scFv, Fab, F(ab')$_2$ or Fv or other modified forms thereof, may be administered to a recipient in the form of serum, plasma, blood, colostrum, and the like. However, the antibodies may also be isolated from serum, plasma, blood, colostrum, and the like, using known methods for later use in a concentrated or reconstituted form. Passive immunization preparations may be particularly advantageous for the treatment of acute systemic illness, or passive immunization of young animals that failed to receive adequate levels of passive immunity through maternal colostrum. Antibodies useful for passive immunization may also be useful to conjugate to various drugs or antibiotics that could be directly targeted to bacteria expressing during a systemic or localized infection a polypeptide of the present invention.

Animal models, in particular pig models, are available for experimentally evaluating the compositions of the present invention. These mouse models are commonly accepted models for the study of disease caused by *H. parasuis*.

The present invention provides kits. A kit may include a polypeptide described herein (when detecting antibody to an OppA polypeptide), an antibody described herein (for detecting the presence of an *H. parasuis* or an OppA polypeptide), a primer pair as described herein (when amplifying a polynucleotide), or a probe (when detecting a polynucleotide by hybridization) in a suitable packaging material in an amount sufficient for at least one assay. Optionally, other reagents such as buffers and solutions, external positive or negative controls, and the like, needed to practice the invention are also included. Instructions for use of the packaged polypeptide, antibody, or primer pair may also be included.

The kits typically include packaging material, which refers to one or more physical structures used to house the contents of the kit. The packaging material can be constructed by well-known methods, preferably to provide a sterile, contaminant-free environment. The packaging material may have a marking that indicates the contents of the kit. In addition, the kit contains instructions indicating how the materials within the kit are employed. As used herein, the term "package" refers to a solid matrix or material such as glass, plastic, paper, foil, and the like.

"Instructions" typically include a tangible expression describing the various methods of the present invention, including sample preparation conditions, detection conditions, amplification conditions, and the like.

The present invention is illustrated by the following examples. It is to be understood that the particular examples, materials, amounts, and procedures are to be interpreted broadly in accordance with the scope and spirit of the invention as set forth herein.

Example 1

Figure 2:
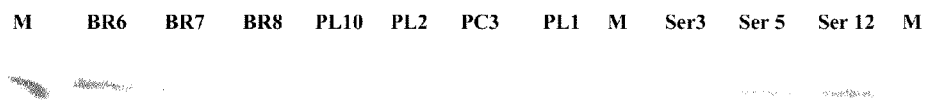
FIG. 2. Detection of the immunogenic species-specific antigen in 7 *Haemophilus parasuis* field strains obtained from an outbreak from brain (BR), pleura (PL), and pericardium (PC) and 3 *Haemophilus parasuis* references strains (Ser3, serotype 3; Ser5, serotype 5; and Ser12, serotype 12) by western blot of whole cell protein profiles. M, molecular weight marker.

Twenty pigs involved in an *H. parasuis* outbreak were selected based on clinical signs (fever >105° F., respiratory distress, lameness, CNS signs) for necropsy and *H. parasuis* isolation (n=10) or for antibiotic treatment to produce convalescent sera (n=10). Whole cell proteins obtained from *H. parasuis* isolates recovered from diseased pigs were probed with convalescent serum using Western blot. This serum was used for western blot analysis of the whole cell protein profiles of the outbreak strains and 13 *H. parasuis* reference strains. Convalescent serum from these pigs strongly reacted to a protein of estimated molecular weight of 52 kDa in all *H. parasuis* strains tested. This protein was identified in all *H. parasuis* reference strains tested (FIG. 1) and in all field strains obtained from brain, pleura, and pericardium during an outbreak (FIG. 2). Pre-colostrum serum obtained from a 1 day-old piglet was used as a negative control in all Western blots.

Figure 3:
FIG. 3. Specificity testing using serum from a piglet obtained prior to colostrum suckling. M, molecular weight marker.
Figure 4:
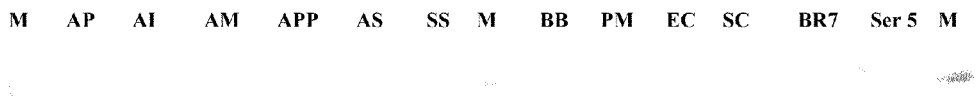
FIG. 4. Specificity testing by western blot of whole cell protein profiles using serum from a convalescent pig that survived a *H. parasuis* outbreak. AP, *Actinobacillus porcinus*; AI, *Actinobacillus indolicus*; AM, *Actinobacillus minor*; APP, *Actinobacillus pleuropneumoniae*; AS, *Actinobacillus suis*; SS, *Streptococcus suis*; BB, *Bordetella bronchiseptica*; PM, *Pasteurella multocida*; EC, *Escherichia coli*; SC, *Salmonella choleraesuis*; BR7, a *Haemophilus parasuis* strains isolated from brain; and Ser 5, reference strain for serotype 5. M, molecular weight marker.

The 52 kDa protein was not detected by western blot when we used serum collected from a piglet prior to colostrum ingestion (FIG. 3). This indicated that there was no non-specific detection of the 52 kDa protein by swine serum. Convalescent serum obtained from 10 pigs involved in an *H. parasuis* outbreak failed to react with a 52 kDa protein in other bacterial pathogens commonly isolated from swine including *Actinobacillus porcinus, Actinobacillus indolicus, Actinobacillus minor, Actinobacillus pleuropneumoniae, Actinobacillus suis, Streptococcus suis, Bordetella bronchiseptica, Pasteurella multocida, Escherichia coli,* and *Salmonella choleraesuis* (FIG. 4). As shown in FIG. 4, the protein was detected in a *Haemophilus parasuis* strain isolated from brain (BR7) and in the reference strain for serotype 5.

Figure 5:
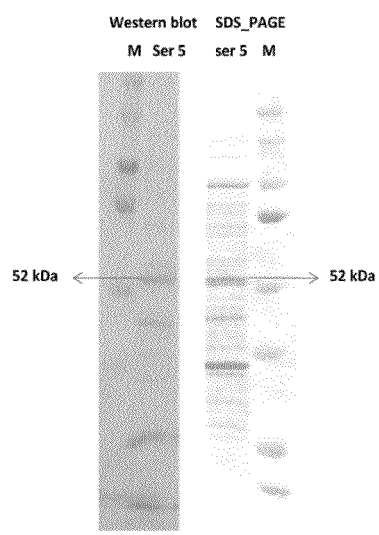
FIG. 5. SDS-PAGE showing 52 kDa protein identified by convalescent sera (western blot) and selected for further identification by sequencing. Ser5, serotype 5; M, molecular weight marker.
Figure 6:
FIG. 6. Oligopeptide permease operon in *Haemophilus parasuis*. The protein identified as described herein is encoded by the OppA segment of this operon.

The 52 kDa proteins obtained from an *H. parasuis* outbreak and serotype 5 reference strains were sequenced and results were blasted using the NCBI database. The protein was consistently identified as Oligopeptide Permease (Opp) (more specifically the OppA) based on sequencing and molecular weight in SDS-PAGE gel (FIGS. 5 and 6). The following are the complete nucleotide and amino acid sequences for the OppA gene and protein of *H. parasuis* that were the closest matches to the sequences generated in this study. These sequences were used to produce and express this protein in *E. coli*.

OppA Nucleotide sequence SEQ ID NO:1, Genbank accession number CP001321, nucleotides 1108151-1109734. The reverse complement of nucleotides 1-1,584 encodes SEQ ID NO:2, where GTG is the start codon:

```
TTATTTACGGCTTACACCAATGAATGACATACCTGTGGTTGATAATGGTT
TAAAGCCATCTAATGCTTTGTTACTCCAAGCTGTTGGAAGTTTACGGTGA
ATAATTGGATAAAGTGCTGCTTCTTCAGCAATGATGTTAATCGCTTTACC
CCAAATTTCACGTGCTTCTGCCGGAGTTTTCGCAGCCACCGCAGCGTCAA
GAAGTTTTTGAACTTCCGCATATTCAGGTGTATTTGACCAGCGGAAACGT
TTTTTCGGCCATACATCACCACGGTACCACCAGCTTAATAATAAGTCTAA
GTCGTTACCGAATACTGATGGGTCACCTGGTGCGATTAATACTTCAAAGT
TACCTGCATCAACACCGTCATTGTATGGTGATTGTGAAGCGATGTTTGTC
ACTTTTACACCAGGGATCTTGTTCCAGTCTTCAAGGATCATTTGAACAGA
GTCCACTACCCATTTATGTGCGGTTGAACGTGTTGTAAACTCAAGTTTAT
CTACACCCGCTTCTTTCAACAATGCAGCCGCTTTTTCGGATCGAAATCA
TAGACTGTTGAGGCTTTCACATAGTCTGGGTGAGAGTCTTGAACATAAGA
TGTCGCAGGTTTTGCGTTGCCTAAGAACACCACATCAACTAATTTTTGTG
TATCAATTGCATATTGTAATGCTTGACGTACTTTCTTGTTGTTAAACGGT
GCTTTTTCACAGTTAAACATTAAGAAAATTAAGCCGAATGATTGCACTGA
TTCTACAGCTGCTTTACGTTTTAAGCGATCCGCATCTAAGTAAGGTACGT
TTTCAATCGCTTGTACACGACCTGACTCTTGTGCTGCAACACGTGCTGCG
TCATCAAAGAGTAAGAACCATGTCATTTTTTCAACAGTTGCAGGATATGG
ACCTGTGTAAGCAGGGTTTGCTTCAAATACGATACGGTCATCTTTGACTG
CTGAAACAAATTTATATGGACCAGTACCAGCAGGGTTTGCATCAAAGACT
GATTGACCTTGAGCTTCAATTAATGCTTTTGGTACTATTTTGATAATGGT
TAAACGTTCTTTGAATAATGCAAATGGATATTTCAATTTAAATTCAACTG
TTTTTTGATCCACTGCAGTGACTGATTTAATGAATGGGATGAATTGTGCA
AAGAGTGATTTTGTATTTGGATCTAATACACGCTCAAATGAAAACACAAC
ATCAGCACTGGTTACTGCTGAACCGTTATGGAATACCGCACCGTCACGTA
AAGTGATGCGATAAGTTACATCGTCAACTTTTTCTGGTTCTTTCGCTGCA
AGTGCTAGATATGGCTGGCGAGTTGCTGGGTGTAAATCAACTAAACCTTC
AAAAATGTGGATATTAGCCGCCATTGAAGATGCACCAGTTGAACTCATTG
GGTCAAAACCCGTTGAAATCGGATAAGCAATACCTGTTTCGATAGTTGAA
CCTTTTGCTGGTGCAGCATAAGCCTGAGAAGCAAAAGTACCGATTGAACC
TGAGAATGCTAAACCAGCACCAACACCTGCAACTAATTTCATAAAGCCAC
GGCGAGATTCATTGTGTTCAAAATGTTTAGTCAC
```

OppA protein sequence SEQ ID NO:2 (Genbank accession number ACL32731:

```
MTKHFEHNESRRGFMKLVAGVGAGLAFSGSIGTFASQAYAAPAKGSTIET
GIAYPISTGFDPMSSTGASSMAANIHIFEGLVDLHPATRQPYLALAAKEP
EKVDDVTYRITLRDGAVFHNGSAVTSADVVFSFERVLDPNTKSLFAQFIP
FIKSVTAVDQKTVEFKLKYPFALFKERLTIIKIVPKALIEAQGQSVFDAN
PAGTGPYKFVSAVKDDRIVFEANPAYTGPYPATVEKMTWFLLFDDAARVA
AQESGRVQAIENVPYLDADRLKRKAAVESVQSFGLIFLMFNCEKAPFNNK
KVRQALQYAIDTQKLVDVVFLGNAKPATSYVQDSHPDYVKASTVYDFDPK
KAAALLKEAGVDKLEFTTRSTAHKWVVDSVQMILEDWNKIPGVKVTNIAS
QSPYNDGVDAGNFEVLIAPGDPSVFGNDLDLLLSWWYRGDVWPKKRFRWS
NTPEYAEVQKLLDAAVAAKTPAEAREIWGKAINIIAEEAALYPIIHRKLP
TAWSNKALDGFKPLSTTGMSFIGVSRK
```

Example 2

This example details the development of a *Haemophilus parasuis* OppA ELISA test and validation of the new test using serum samples obtained from different swine herds. Additional serum samples have been tested and validation of the test continues. The samples reported here were carefully planned and demonstrate uses for the ELISA test. Results were evaluated based on sample to positive ratios (S/P). The conclusions were made based on the trends detected. The main conclusions obtained so far include:

Non-vaccinated, clinically healthy, colonized pigs do not develop antibodies against *Haemophilus parasuis* OppA;

Pigs that have survived the peak of *Haemophilus parasuis*-related nursery mortality develop high titers of anti-OppA IgG; and Pigs need to be systemically exposed to *Haemophilus parasuis* to develop anti-OppA antibodies.

Expression and Purification of OppA

The OppA polypeptide was expressed and purified by GenScript Corp. (Piscataway, N.J.). Briefly, a coding region encoding the OppA polypeptide sequence was optimized for expression in *E. coli*, subcloned in-frame to three different polynucleotides, each of which resulted in a polypeptide that included an N-terminal region with a polyhistidine tag, SEQ ID NO:2, and a protease cleavage site between the N-terminal region and SEQ ID NO:2 (FIG. 13). The nucleotide sequence of the coding region optimized for expression in *E. coli* is shown in FIG. 14 (SEQ ID NO:9). The protease cleavage sites were ENLYFQG (SEQ ID NO:10), which is cleaved by TEV protease, and DDDDK (SEQ ID NO:11), which is cleaved by enterokinase.

The polypeptide was expressed and purified using routine methods, and the N-terminal region and tag was removed by cleavage with the appropriate protease. The polypeptide was >90% pure as estimated by Coomassie blue-stained SDS-PAGE, and the yield was 0.8 mg (0.3 mg/ml in 50 mM Tris-HCl, 300 mM NaCl, pH 8.0) tag-free polypeptide prepared from 1 liter of culture. The polypeptide was expressed as a soluble faun.

ELISA Protocol

OppA was cloned and expressed in *Escherichia coli* and the purified antigen was used to coat ELISA plates for detection of swine anti-Haemophilus parasuis OppA antibodies using an indirect ELISA system. Purified OppA was diluted in carbonate buffer to produce a solution with a concentration of 1 µg/ml. Each well of the ELISA plates were coated with 100 µl of carbonate buffer (15 mM $NaCO_3$, 35 mM $NaHCO_3$, pH 9.6) incubated overnight at 4° C. Prior to adding serum samples to the plates, non-specific binding sites were inactivated by adding 300 µl of blocking solution (PBST and 0.05% non-fat dry milk (ph 9.6)) to each well and incubating the ELISA plates for 2 h at room temperature. Following blocking of non-specific binding sites, the ELISA plates were washed with phosphate buffered saline Tween-20 (PBST: phosphate buffered saline (pH 7.4) and 0.05% Tween 20) for three consecutive times. Porcine serum samples were diluted 1:50 in 5% non-fat dry milk (NFDM) in PBST and 100 µl of this solution were added to each well on the plates. A known positive and a known negative sample based on western blot analysis were added as controls. The plates containing porcine serum samples were incubated at room temperature for 1 h. Following primary antibody binding, the ELISA plates were again washed with a PBST for three consecutive times. Once the excess of washing solution was eliminated, commercially available goat anti-swine antibodies (secondary antibodies) labeled with peroxidase were diluted at 1:100,000 in 5% NFDM in PBST and 100 µl of this solution was added to the ELISA plates. Plates containing the secondary antibody were incubated at room temperature for 1 h. After the incubation period was complete, ELISA plates were washed once again three consecutive times using PBST. Following the washing step to remove unbound secondary antibodies, 100 µl of a solution containing equal parts of TMB peroxidase substrate (3,3',5,5'-tetramethylbenzidine at a concentration of 0.4 g/L in an organic base) and peroxidase ($H_2O_2$ at a concentration of 0.02% in a citric acid buffer) were added to each well for detection of bound secondary goat anti-swine antibodies. The reaction was quenched by adding 100 µl of 1 M phosphoric acid solution to each well. Optical densities obtained for each well were read at 450 nm using a microplate reader. Optical densities were used to calculate sample to positive (S/P) ratios for each sample tested.

Testing of Field Serum Samples

Figure 7:
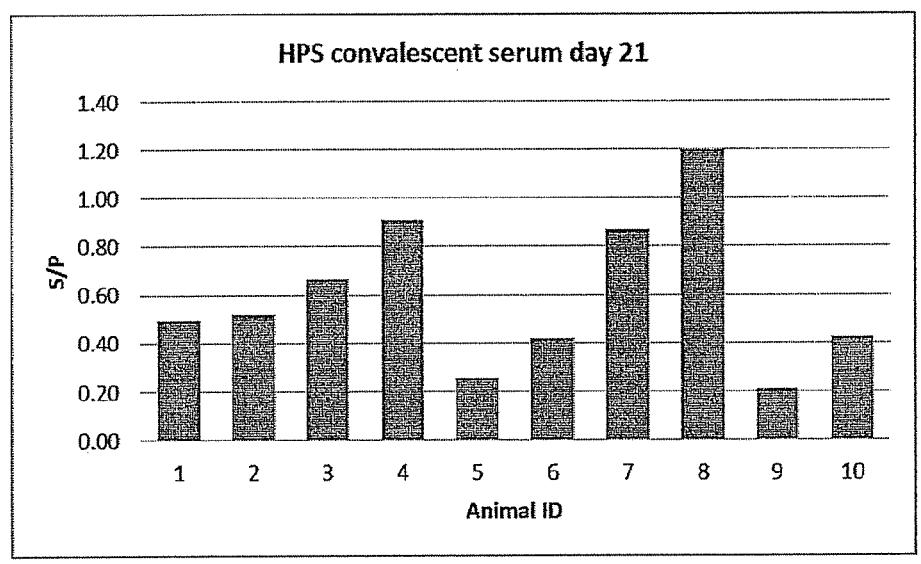
FIG. 7. Anti-OppA antibodies sample to positive (S/P) ratios obtained for serum samples collected from 10 pigs that survived a *Haemophilus* parasuis outbreak.

Convalescent Pigs:

The same serum samples that were used to discover and characterize the antigenicity of the *Haemophilus parasuis* OppA were tested using the developed OppA ELISA test. Convalescent serum samples were collected from 10 pigs that had survived a *Haemophilus parasuis* outbreak. The S/P ratios obtained for convalescent pigs varied from 0.21 to 1.2 (FIG. 7). All convalescent pigs had antibodies against the *Haemophilus parasuis* OppA antigen, which was in agreement with previously obtained western blot results. Eight out of 10 convalescent pigs had S/P ratios above 0.4 (FIG. 7). These results indicate that pigs that have survived a *Haemophilus parasuis* outbreak and had a systemic contact with the agent respond serologically to the OppA protein with production of anti-OppA IgG.

Figure 8A:
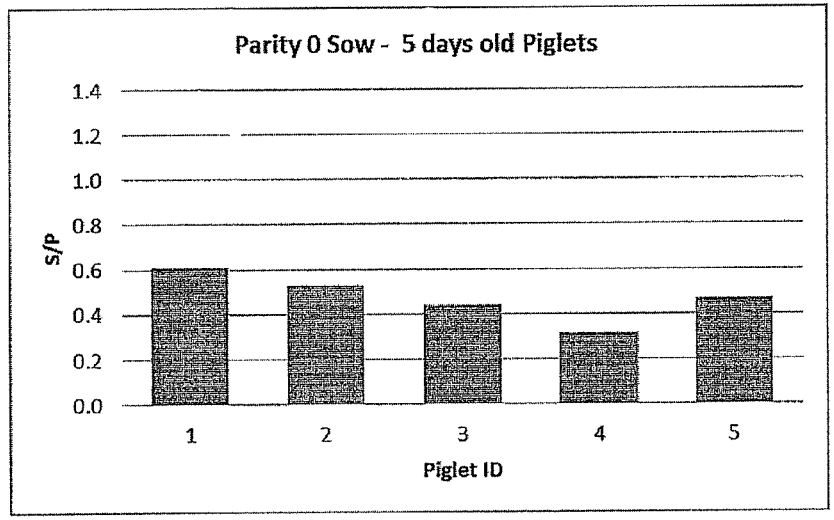
FIG. 8. Anti-OppA antibodies sample to positive (S/P) ratios obtained for serum samples collected from 5 (A) and 19 (B) day old piglets.
Figure 8B:
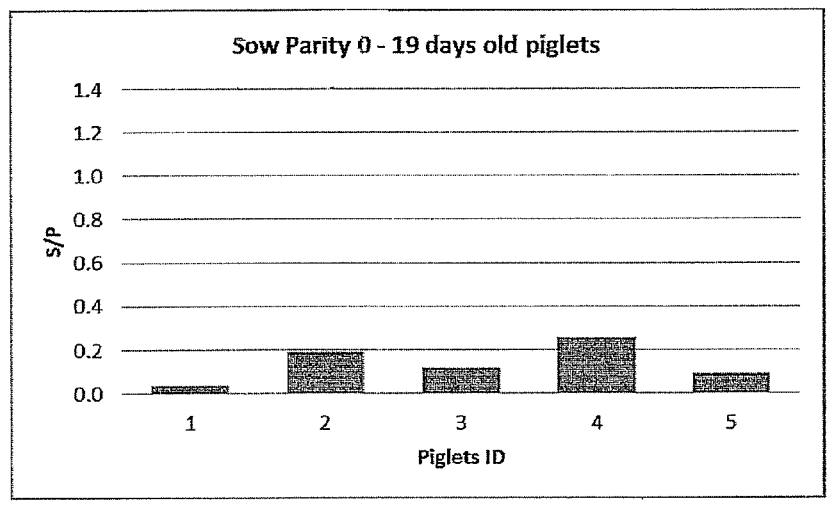

Decay of Maternal Immunity:

In order to evaluate the decay of *Haemophilus parasuis*-related maternal immunity, serum samples were collected from piglets at 5 and 19 days of age. At 5 days of age, S/P ratios varied from 0.32 to 0.61 (FIG. 8A), indicating the presence of maternally-derived anti-OppA antibodies. At 19 days of age, maternal antibodies were substantially reduced, with S/P ratios varying from 0.04 to 0.26 (FIG. 8B). These results demonstrate the use of the *Haemophilus parasuis* OppA ELISA to monitor decay of maternal immunity in young piglets. This information is useful to identify the window of susceptibility between decay of maternal immunity and development of active immune response. Furthermore, monitoring of decay of maternal antibodies can be used for strategic placement of piglet vaccination. Tracking of maternal immunity is also useful to evaluate the efficacy of sow vaccination.

Figure 9A:
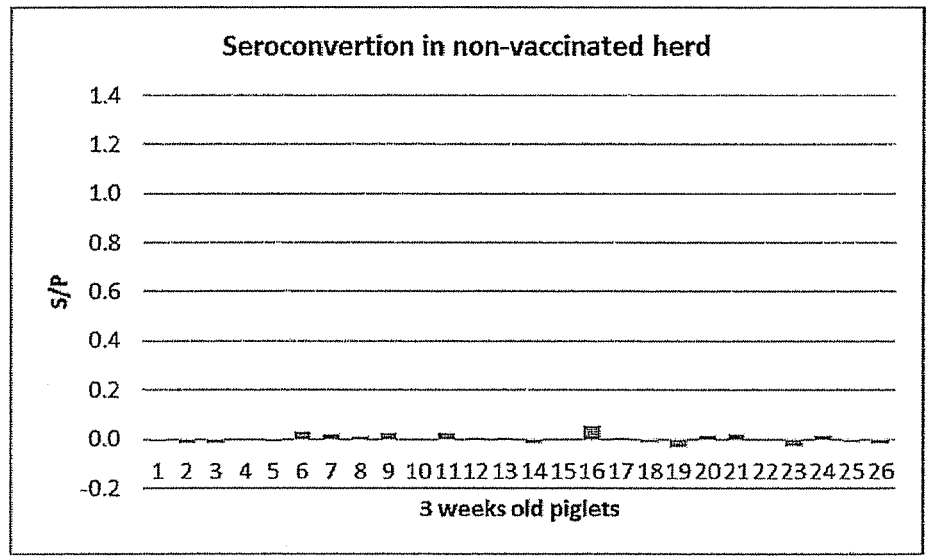
FIG. 9. (A) Anti-OppA antibodies sample to positive (S/P) ratios obtained for 26 piglets at 3 weeks of age. All pigs lacked antibodies against *Haemophilus parasuis* OppA. This profile coincides with decay of maternal immunity and absence of active immunity in this population. (B) Anti-OppA S/P ratios obtained for 30 pigs at 8 weeks of age in the same population. All pigs had S/P ratios above 0.1, indicating the development of active immune response following systemic contact with *Haemophilus parasuis* after surviving the peak of nursery mortality. Cross-sectional sampling.
Figure 9B:
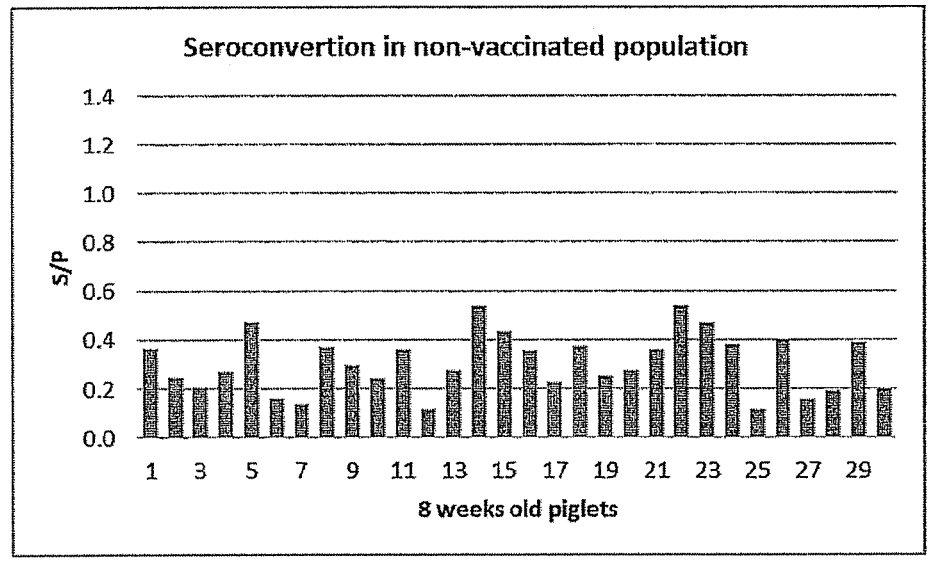

Serum Profiling of a Naturally Exposed, Non-Vaccinated Population (Cross-Sectional Sampling):

Serum samples were collected from pigs at 3 and 8 weeks of age. These pigs were colonized with *Haemophilus parasuis* and were experiencing *Haemophilus parasuis*-related mortality at 5 to 6 weeks of age. Pigs were not vaccinated at the time of sampling and were obtained from non-vaccinated sows. The S/P ratios obtained for 3 week old pigs varied from −0.03 to 0.05, indicating that 3 week old pigs lacked anti-OppA antibodies (FIG. 9A) even in the presence of colonization. The S/P ratios obtained for 8 week old pigs (2-3 weeks after the peack of nursery mortality) varied from 0.12 to 0.54, indicating that pigs developed anti-OppA antibodies after they went through infection and survive the peak of *Haemophilus parasuis*-related mortality (FIG. 9B). These results demonstrate the use of the *Haemophilus parasuis* OppA ELISA to detect sysemic contact with *Haemophilus parasuis* in the absence of vaccination. Clinically healthy colonized pigs do not develop antibodies against *Haemophilus parasuis* OppA.

Figure 10A:
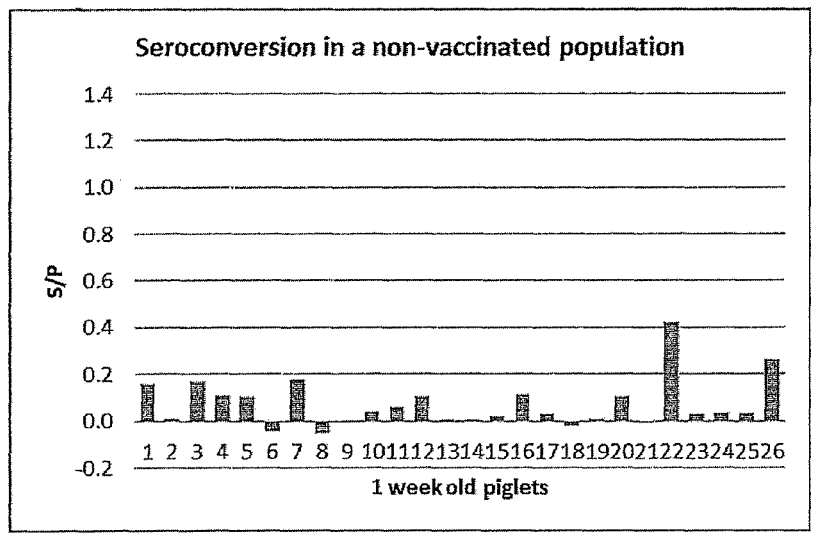
FIG. 10. Anti OppA S/P ratios obtained from 26 pigs from a naturally exposed, colonized, non-vaccinated population at 1 (A) and 9 (B) weeks of age. Some maternal immunity was evident at 1 week-old, whereas seroconversion was evident at 9 weeks of age, after the peak of *Haemophilus parasuis*-related mortality. Longitudinal sampling.
Figure 10B:
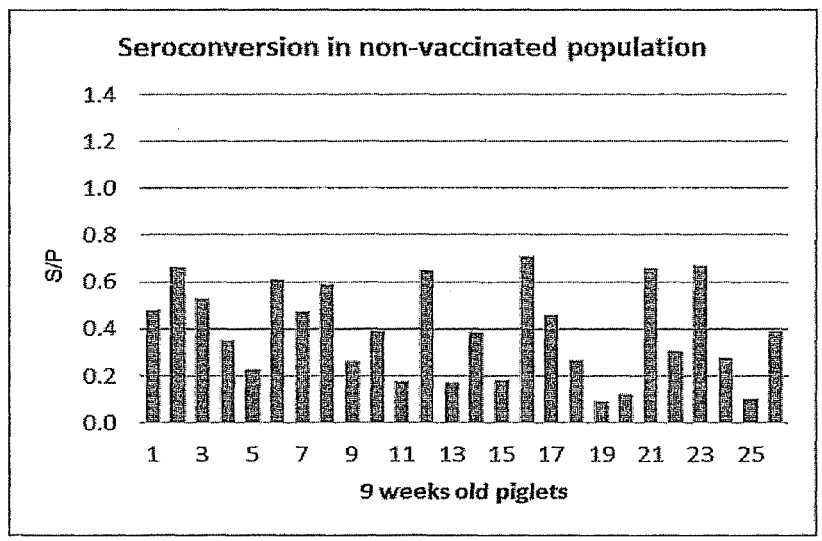

Serum Profiling of a Naturally Exposed, Non-Vaccinated Population (Longitudinal Sampling):

Serum samples were collected from 26 pigs at 3 and 8 weeks of age. Pigs were not vaccinated at time of sampling and were obtained from non-vaccinated gilts. The S/P ratios obtained for 3 week old pigs varied from −0.04 to 0.42, indicating that 1 week old pigs had low levels of anti-OppA maternal antibodies in this population (FIG. 10A). The S/P ratios obtained for 9 week old pigs (2-3 weeks after the peak of nursery mortality) varied from 0.09 to 0.67, indicating that pigs developed anti-OppA antibodies after they went through infection and survived the peak of *Haemophilus parasuis*-related mortality (FIG. 10B). These results further demonstrate the use of the *Haemophilus parasuis* OppA ELISA to detect systemic contact with *Haemophilus parasuis* in the absence of vaccination.

Example 3

Experimental Design:

Conventional healthy pigs are randomly allocated into 2 groups. For instance, twenty-two 3-week old conventional healthy pigs are randomly allocated into 2 rooms with 11 pigs per group (Table 1). Group 1 is vaccinated intramuscularly with the OppA subunit vaccine on days 0 and 14 of the experiment. Group 2 is vaccinated with adjuvant only and will remain as the non-vaccinated control. All pigs are challenged with a serotype 5 *H. parasuis* strain at the day 28 of the experiment and necropsied at day 35. The sample size used is adequate to detect significant differences between the proportion of affected pigs in the unvaccinated group (expected 80%) and vaccinated group (expected 20%) with 95% confidence and 80% power (Sergeant, ESG, 2009. Epitools epidemiological calculators. AusVet Animal Health Services and Australian Biosecurity Cooperative Research Centre for Emerging Infectious Disease. Available online at the AusVet Animal Health Services internet site).

All pigs are bled before and after vaccination. For instance, pigs may be bled on days 0 (prior to 1st vaccination), 14 (prior to 2nd vaccination), 28 (prior to challenge) and 35 (survivals after challenge). Serum samples are tested for PRRS virus by PCR on day 0. Clinical signs, including rectal temperature, are recorded at arrival, prior to challenge, and following challenge, for instance, weekly prior to challenge, and daily following challenge. Nasal swabs to detect colonization are collected and tested by PCR before and after vaccination, for instance, on days 0 (baseline) and 28 (effect of vaccination on clearance of *H. parasuis* from tonsils). Lesions observed at necropsy are recorded and graded according to severity. Thoracic and peritoneal serous surfaces are tested for the presence of *H. parasuis* by isolation and PCR.

TABLE 1

Example of experimental design for vaccination and challenge.

| Group | Number of pigs | Vaccination | Challenge |
|---|---|---|---|
| 1 | 11 | Yes | Serotype 5 |
| 2 | 11 | No | Serotype 5 |

Vaccination: Highly purified (>90%) *H. parasuis* OppA is used as antigen. A prototype vaccine is produced using an OppA concentration of, for instance, 200 μg/ml in oil-in-water adjuvant (Triagen®—currently used to produce autogenous *H. parasuis* vaccines). Pigs are vaccinated twice (for instance, at days 0 and 14) by the intramuscular route using a 1 ml dose (current route and volume used for most swine vaccines).

Challenge: *Haemophilus parasuis* serotype 5, ahighly virulent reference strain among U.S. swine herds, is used for challenge (Table 1). The serotype 5 reference strain has been originally isolated from the brain of a pig with systemic *H. parasuis* infection and carries virulence-associated genes based on VtaA multiplex PCR (Olvera et al., 2010, Vet. Res., 5-6; 41(3):26). The challenge strain is passaged onto 10 days embryonated chicken eggs prior to challenge. This method has been shown to mimic in vivo conditions and increase capsule production, which is also a virulence factor (Oliveira, 2003, *Haemophilus parasuis*: epidemiology, diagnosis and control. Saint Paul: University of Minnesota, Ph. D. thesis). Pigs are challenged intravenously (6 pigs per group) and intranasaally (5 pigs per group) at day 28 of the experiment with 1 ml of pure culture in exponential growth phase (Hoffmann et al., 2002, Dtsch. Tierarztl. Wochenschr., 109(6):271-276). Following challenge, pigs are monitored closely and euthanized as soon as evident clinical disease is observed (fever, respiratory distress, lameness, and/or CNS signs).

Serological testing: Serum samples obtained at days 0, 14, 28, and 35 are tested by the OppA ELISA test described in Example 2. Seroconversion will be evaluated by comparing S/P ratios before and after vaccination.

Statistical analysis: An affected pig is defined as a pig showing clinical signs (CNS signs, respiratory distress, and/or lameness), fever (temperature over 105° F.) and/or gross lesions of serositis. Because of the small sample size, non-parametric statistics are used. Specifically, Fisher's exact test is used to compare categorical data (such as mortality, proportion of affected pigs, rate of isolation of *H. parasuis*) between vaccinated and unvaccinated groups. Mann-Whitney U test is used to compare continuous data (distribution of ELISA s/p values).

The complete disclosure of all patents, patent applications, and publications, and electronically available material (including, for instance, nucleotide sequence submissions in, e.g., GenBank and RefSeq, and amino acid sequence submissions in, e.g., SwissProt, PR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method for detecting the presence of an antibody against *Haemophilus parasuis* in a biological sample from an animal, comprising:
   mixing the biological sample from the animal with a polypeptide under conditions suitable for formation of an antigen: antibody complex, said biological sample containing an antibody against *Haemophilus parasuis*, wherein the polypeptide comprises an amino acid sequence having at least 80% identity with SEQ ID NO:2, wherein the antibody binds to an oligopeptide permease OppA of *Haemophilus parasuis* as set forth in SEQ ID NO:2, wherein the polypeptide has oligopeptide permease activity, wherein the animal is selected from the group consisting of porcine, avian, bovine, caprine, ovine, equine, murine, human, and a companion animal; and
   detecting the complex, wherein the presence of the complex indicates the animal has antibody that specifically binds to the polypeptide.

2. The method of claim 1 wherein the presence of the complex indicates the animal has been infected with *Haemophilus parasuis*.

3. The method of claim 1 wherein the biological sample comprises serum, oral fluid, colostrum, lung lavage, bronchial lavage, tracheal lavage, or nasal lavage.

4. The method of claim 1 wherein the polypeptide is bound to a surface.

5. The method of claim 2 wherein the *H. parasuis* is a serotype chosen from 1, 2, 3, 4, 5, 6, 7, 8, 9, 10, 11, 12, 13, 14, and 15.

6. The method of claim 2 wherein the *H. parasuis* is a non-typable serotype.

7. The method of claim 1 wherein the antibody present in the biological sample is a first antibody and the complex is a first complex, and wherein the detecting comprises contacting the first antibody with a second antibody that specifically binds the first antibody and forms a second complex, and detecting the second complex.

8. The method of claim 1 wherein the polypeptide comprises an amino acid sequence having at least 90% identity with SEQ ID NO:2.

9. A method for detecting the presence of an antibody against *Haemophilus parasuis* in a biological sample from an animal, comprising:
   mixing the biological sample from the animal with a polypeptide under conditions suitable for formation of an antigen: antibody complex, said biological sample containing an antibody against *Haemophilus parasuis*, wherein the polypeptide comprises an amino acid sequence having at least 80% identity with SEQ ID NO:2, wherein the antibody detected is an antibody that binds to an oligopeptide permease OppA of *Haemophilus parasuis* as set forth in SEQ ID NO:2, and does not bind to an oligopeptide permease of *Actinobacillus pleuropneumoniae* as set forth in SEQ ID NO:4 wherein the animal is selected from the group consisting of porcine, avian, bovine, caprine, ovine, equine, murine, human, and a companion animal; and
   detecting the complex, wherein the presence of the complex indicates the animal has antibody that specifically binds to the polypeptide.

* * * * *

SEQUENCE LISTING

```
<160> NUMBER OF SEQ ID NOS: 14

<210> SEQ ID NO 1
<211> LENGTH: 1584
<212> TYPE: DNA
<213> ORGANISM: Haemophilus parasuis

<400> SEQUENCE: 1
ttatttacgg cttacaccaa tgaatgacat acctgtggtt gataatggtt taaagccatc      60
taatgctttg ttactccaag ctgttggaag tttacggtga ataattggat aaagtgctgc     120
```

-continued

```
ttcttcagca atgatgttaa tcgctttacc ccaaatttca cgtgcttctg ccggagtttt    180
cgcagccacc gcagcgtcaa gaagttttg aacttccgca tattcaggtg tatttgacca    240
gcggaaacgt ttttcggcc atacatcacc acggtaccac cagcttaata ataagtctaa    300
gtcgttaccg aatactgatg ggtcacctgg tgcgattaat acttcaaagt tacctgcatc    360
aacaccgtca ttgtatggtg attgtgaagc gatgtttgtc acttttacac cagggatctt    420
gttccagtct tcaaggatca tttgaacaga gtccactacc catttatgtg cggttgaacg    480
tgttgtaaac tcaagtttat ctacacccgc ttctttcaac aatgcagccg ctttttcgg    540
atcgaaatca tagactgttg aggctttcac atagtctggg tgagagtctt gaacataaga    600
tgtcgcaggt tttgcgttgc ctaagaacac cacatcaact aatttttgtg tatcaattgc    660
atattgtaat gcttgacgta ctttcttgtt gttaaacggt gctttttcac agttaaacat    720
taagaaaatt aagccgaatg attgcactga ttctacagct gctttacgtt ttaagcgatc    780
cgcatctaag taaggtacgt tttcaatcgc ttgtacacga cctgactctt gtgctgcaac    840
acgtgctgcg tcatcaaaga gtaagaacca tgtcattttt tcaacagttg caggatatgg    900
acctgtgtaa gcagggtttg cttcaaatac gatacggtca tctttgactg ctgaaacaaa    960
tttatatgga ccagtaccag cagggtttgc atcaaagact gattgacctt gagcttcaat   1020
taatgctttt ggtactattt tgataatggt taaacgttct ttgaataatg caaatggata   1080
tttcaattta aattcaactg ttttttgatc cactgcagtg actgatttaa tgaatgggat   1140
gaattgtgca aagagtgatt ttgtatttgg atctaataca cgctcaaatg aaaacacaac   1200
atcagcactg gttactgctg aaccgttatg gaataccgca ccgtcacgta agtgatgcg    1260
ataagttaca tcgtcaactt tttctggttc tttcgctgca agtgctagat atggctggcg   1320
agttgctggg tgtaaatcaa ctaaaccttc aaaaatgtgg atattagccg ccattgaaga   1380
tgcaccagtt gaactcattg ggtcaaaacc cgttgaaatc ggataagcaa tacctgtttc   1440
gatagttgaa cctttgctg gtgcagcata agcctgagaa gcaaaagtac cgattgaacc    1500
tgagaatgct aaaccagcac caacacctgc aactaatttc ataaagccac ggcgagattc   1560
attgtgttca aaatgtttag tcac                                          1584
```

<210> SEQ ID NO 2
<211> LENGTH: 527
<212> TYPE: PRT
<213> ORGANISM: Haemophilus parasuis

<400> SEQUENCE: 2

```
Met Thr Lys His Phe Glu His Asn Glu Ser Arg Arg Gly Phe Met Lys
1               5                   10                  15

Leu Val Ala Gly Val Gly Ala Gly Leu Ala Phe Ser Gly Ser Ile Gly
            20                  25                  30

Thr Phe Ala Ser Gln Ala Tyr Ala Ala Pro Ala Lys Gly Ser Thr Ile
        35                  40                  45

Glu Thr Gly Ile Ala Tyr Pro Ile Ser Thr Gly Phe Asp Pro Met Ser
    50                  55                  60

Ser Thr Gly Ala Ser Ser Met Ala Ala Asn Ile His Ile Phe Glu Gly
65                  70                  75                  80

Leu Val Asp Leu His Pro Ala Thr Arg Gln Pro Tyr Leu Ala Leu Ala
                85                  90                  95

Ala Lys Glu Pro Glu Lys Val Asp Asp Val Thr Tyr Arg Ile Thr Leu
            100                 105                 110
```

-continued

Arg Asp Gly Ala Val Phe His Asn Gly Ser Ala Val Thr Ser Ala Asp
115                 120                 125

Val Val Phe Ser Phe Glu Arg Val Leu Asp Pro Asn Thr Lys Ser Leu
130                 135                 140

Phe Ala Gln Phe Ile Pro Phe Ile Lys Ser Val Thr Ala Val Asp Gln
145                 150                 155                 160

Lys Thr Val Glu Phe Lys Leu Lys Tyr Pro Phe Ala Leu Phe Lys Glu
                165                 170                 175

Arg Leu Thr Ile Ile Lys Ile Val Pro Lys Ala Leu Ile Glu Ala Gln
                180                 185                 190

Gly Gln Ser Val Phe Asp Ala Asn Pro Ala Gly Thr Gly Pro Tyr Lys
        195                 200                 205

Phe Val Ser Ala Val Lys Asp Asp Arg Ile Val Phe Glu Ala Asn Pro
210                 215                 220

Ala Tyr Thr Gly Pro Tyr Pro Ala Thr Val Glu Lys Met Thr Trp Phe
225                 230                 235                 240

Leu Leu Phe Asp Asp Ala Ala Arg Val Ala Ala Gln Glu Ser Gly Arg
                245                 250                 255

Val Gln Ala Ile Glu Asn Val Pro Tyr Leu Asp Ala Asp Arg Leu Lys
                260                 265                 270

Arg Lys Ala Ala Val Glu Ser Val Gln Ser Phe Gly Leu Ile Phe Leu
275                 280                 285

Met Phe Asn Cys Glu Lys Ala Pro Phe Asn Asn Lys Lys Val Arg Gln
290                 295                 300

Ala Leu Gln Tyr Ala Ile Asp Thr Gln Lys Leu Val Asp Val Val Phe
305                 310                 315                 320

Leu Gly Asn Ala Lys Pro Ala Thr Ser Tyr Val Gln Asp Ser His Pro
                325                 330                 335

Asp Tyr Val Lys Ala Ser Thr Val Tyr Asp Phe Asp Pro Lys Lys Ala
                340                 345                 350

Ala Ala Leu Leu Lys Glu Ala Gly Val Asp Lys Leu Glu Phe Thr Thr
        355                 360                 365

Arg Ser Thr Ala His Lys Trp Val Val Asp Ser Val Gln Met Ile Leu
370                 375                 380

Glu Asp Trp Asn Lys Ile Pro Gly Val Lys Val Thr Asn Ile Ala Ser
385                 390                 395                 400

Gln Ser Pro Tyr Asn Asp Gly Val Asp Ala Gly Asn Phe Glu Val Leu
                405                 410                 415

Ile Ala Pro Gly Asp Pro Ser Val Phe Gly Asn Asp Leu Asp Leu Leu
                420                 425                 430

Leu Ser Trp Trp Tyr Arg Gly Asp Val Trp Pro Lys Lys Arg Phe Arg
        435                 440                 445

Trp Ser Asn Thr Pro Glu Tyr Ala Glu Val Gln Lys Leu Leu Asp Ala
450                 455                 460

Ala Val Ala Ala Lys Thr Pro Ala Glu Ala Arg Glu Ile Trp Gly Lys
465                 470                 475                 480

Ala Ile Asn Ile Ile Ala Glu Glu Ala Ala Leu Tyr Pro Ile Ile His
                485                 490                 495

Arg Lys Leu Pro Thr Ala Trp Ser Asn Lys Ala Leu Asp Gly Phe Lys
                500                 505                 510

Pro Leu Ser Thr Thr Gly Met Ser Phe Ile Gly Val Ser Arg Lys
        515                 520                 525

-continued

<210> SEQ ID NO 3
<211> LENGTH: 1575
<212> TYPE: DNA
<213> ORGANISM: Actinobacillus pleuropneumoniae

<400> SEQUENCE: 3

```
atgacttctc atttttctca taacgactca cgtcgccact tcatgaagct tcttgccggt      60
gtcggagcag gctttgcatt ctccggtacc ttaggtactt tctctaataa tgcatttgcc     120
gcagcaggta aaggtattga agcagggatt gcttatccga tctcaaccgg ttttgacccg     180
cttacttcaa gcggtgcatc gtctatggcg gcgaacttac atatttttga aggtttagtg     240
gatttacacc cggcaactcg ccaaccttat ttagctttag cggctaaaga gcctgaacag     300
aaagatgaag taacatacca tattacctta cgtgaagggg caaccttcca cgatggtaaa     360
ccggttacca ccgaagatgt ggtttactcg tttgaacgtg tgttagatcc ggcgaaagcc     420
tcactgttcg ctcaatttat tccgtttatc gcttcggtaa aagcacttga caataaagtg     480
gtcgaattca aattaaaata tccgttcgct ttatttaaag aacgtttaac catcgtcaaa     540
atcgtgccga aacatatcgt agaagccggt caatccgcct ttgatgccaa acctgtcggt     600
tcaggtcctt ataaatttgt ttccgcaacc aaagatgacc gtattgtctt tgaagccaat     660
acctcttata acggtatgta tccggctaaa gtagataaaa tgacgtggtt cttattatca     720
gatgatgccg ctcgtgtaac cgcacaagaa tccggccgtg tacaagcgat tgaatccgta     780
ccgtaccttg atgcggaacg cttaaaacgt aaaggaaaag tggaatcagt acaatctttc     840
ggcttactat tcttaatgtt taactgtgaa aaagcaccgt ttgataaccc gaaagtacgc     900
caggcgttac attatggctt agatacacaa aaattaatcg acattgtatt cttaggcaat     960
gcgaaagcgg caagctctta cgtacaagat acccatcctg attatgtaaa agccgccagc    1020
caatatgatt ttgataaagc gaaagcggaa agcctattag cggaagcggg tatcaaagaa    1080
ttaaaatttg aattacttgc aaccgatcac gcttgggtaa aagaatgtgc gccgcttatt    1140
cttgaatctt ggaatgcgtt aaaaggtgtg aaagtaacgc ttcaacattt acaatccggt    1200
gcgttatacg gcacgcacgt tgataaaggt gcgtttgaag tggttatcgc accgggcgat    1260
ccgtccgtat tcggtaacga cttagactta ttattaagct ggtggtaccg cggtgacgta    1320
tggccgaaac gtcgtttccg ttgggcaaat acgcctgaat atgccgaagt acaaaaatta    1380
ctggatgaag cggcgaaaaa tccggcgggt gcaaaagaag catggaccaa agcaatcaat    1440
attattgccg aacaagtgcc gctttacccg atcgtgcatc gtaaattacc gaccgcatgg    1500
agcgataaat cacttaccga tttccaaccg ttaccgacaa caggcttgtc attcttaggc    1560
gtcggtcgta aataa                                                     1575
```

<210> SEQ ID NO 4
<211> LENGTH: 524
<212> TYPE: PRT
<213> ORGANISM: Actinobacillus pleuropneumoniae

<400> SEQUENCE: 4

```
Met Thr Ser His Phe Ser His Asn Asp Ser Arg Arg His Phe Met Lys
1               5                   10                  15

Leu Leu Ala Gly Val Gly Ala Gly Phe Ala Phe Ser Gly Thr Leu Gly
            20                  25                  30

Thr Phe Ser Asn Asn Ala Phe Ala Ala Ala Gly Lys Gly Ile Glu Ala
        35                  40                  45
```

```
Gly Ile Ala Tyr Pro Ile Ser Thr Gly Phe Asp Pro Leu Thr Ser Ser
     50                  55                  60
Gly Ala Ser Ser Met Ala Ala Asn Leu His Ile Phe Glu Gly Leu Val
 65                  70                  75                  80
Asp Leu His Pro Ala Thr Arg Gln Pro Tyr Leu Ala Leu Ala Ala Lys
                 85                  90                  95
Glu Pro Glu Gln Lys Asp Glu Val Thr Tyr His Ile Thr Leu Arg Glu
                100                 105                 110
Gly Ala Thr Phe His Asp Gly Lys Pro Val Thr Thr Glu Asp Val Val
            115                 120                 125
Tyr Ser Phe Glu Arg Val Leu Asp Pro Ala Lys Ala Ser Leu Phe Ala
130                 135                 140
Gln Phe Ile Pro Phe Ile Ala Ser Val Lys Ala Leu Asp Asn Lys Val
145                 150                 155                 160
Val Glu Phe Lys Leu Lys Tyr Pro Phe Ala Leu Phe Lys Glu Arg Leu
                165                 170                 175
Thr Ile Val Lys Ile Val Pro Lys His Ile Val Glu Ala Gly Gln Ser
            180                 185                 190
Ala Phe Asp Ala Lys Pro Val Gly Ser Gly Pro Tyr Lys Phe Val Ser
        195                 200                 205
Ala Thr Lys Asp Asp Arg Ile Val Phe Glu Ala Asn Thr Ser Tyr Asn
210                 215                 220
Gly Met Tyr Pro Ala Lys Val Asp Lys Met Thr Trp Phe Leu Leu Ser
225                 230                 235                 240
Asp Asp Ala Ala Arg Val Thr Ala Gln Glu Ser Gly Arg Val Gln Ala
                245                 250                 255
Ile Glu Ser Val Pro Tyr Leu Asp Ala Glu Arg Leu Lys Arg Lys Gly
            260                 265                 270
Lys Val Glu Ser Val Gln Ser Phe Gly Leu Leu Phe Leu Met Phe Asn
        275                 280                 285
Cys Glu Lys Ala Pro Phe Asp Asn Pro Lys Val Arg Gln Ala Leu His
290                 295                 300
Tyr Gly Leu Asp Thr Gln Lys Leu Ile Asp Ile Val Phe Leu Gly Asn
305                 310                 315                 320
Ala Lys Ala Ala Ser Ser Tyr Val Gln Asp Thr His Pro Asp Tyr Val
                325                 330                 335
Lys Ala Ala Ser Gln Tyr Asp Phe Asp Lys Ala Lys Ala Glu Ser Leu
            340                 345                 350
Leu Ala Glu Ala Gly Ile Lys Glu Leu Lys Phe Glu Leu Leu Ala Thr
        355                 360                 365
Asp His Ala Trp Val Lys Glu Cys Ala Pro Leu Ile Leu Glu Ser Trp
370                 375                 380
Asn Ala Leu Lys Gly Val Lys Val Thr Leu Gln His Leu Gln Ser Gly
385                 390                 395                 400
Ala Leu Tyr Gly Thr His Val Asp Lys Gly Ala Phe Glu Val Val Ile
                405                 410                 415
Ala Pro Gly Asp Pro Ser Val Phe Gly Asn Asp Leu Asp Leu Leu
            420                 425                 430
Ser Trp Trp Tyr Arg Gly Asp Val Trp Pro Lys Arg Arg Phe Arg Trp
        435                 440                 445
Ala Asn Thr Pro Glu Tyr Ala Glu Val Gln Lys Leu Leu Asp Glu Ala
450                 455                 460
```

-continued

```
Ala Lys Asn Pro Ala Gly Ala Lys Glu Ala Trp Thr Lys Ala Ile Asn
465                 470                 475                 480

Ile Ile Ala Glu Gln Val Pro Leu Tyr Pro Ile Val His Arg Lys Leu
                485                 490                 495

Pro Thr Ala Trp Ser Asp Lys Ser Leu Thr Asp Phe Gln Pro Leu Pro
                500                 505                 510

Thr Thr Gly Leu Ser Phe Leu Gly Val Gly Arg Lys
            515                 520

<210> SEQ ID NO 5
<211> LENGTH: 528
<212> TYPE: PRT
<213> ORGANISM: Actinobacillus minor

<400> SEQUENCE: 5

Met Lys Thr Gln Phe Glu Leu Asn Glu Ser Arg His Phe Met Lys
1               5                   10                  15

Leu Leu Ala Gly Ala Ser Ala Gly Leu Ala Phe Ser Gly Thr Leu Gly
                20                  25                  30

Thr Phe Ser Ala Glu Ala Phe Ala Ser Ala Pro Ala Gly Ser Ser Ile
            35                  40                  45

Glu Ala Gly Ile Ala Tyr Pro Ile Ser Thr Gly Phe Asp Pro Leu Thr
50                  55                  60

Ala Ser Gly Ala Ser Ser Gln Ala Ala Asn Leu His Ile Phe Glu Gly
65                  70                  75                  80

Leu Val Asp Leu His Pro Ala Thr Arg Gln Pro Tyr Leu Ala Leu Ala
                85                  90                  95

Ala Lys Asp Pro Glu Met Lys Asp Asp Val Thr Tyr His Val Thr Leu
                100                 105                 110

Arg Asp Gly Ala Val Phe His Asp Gly Lys Pro Val Thr Thr Glu Asp
            115                 120                 125

Val Val Tyr Ser Phe Glu Arg Val Leu Asp Pro Ala Lys Ala Ser Leu
130                 135                 140

Phe Ala Gln Phe Ile Pro Phe Ile Glu Ser Val Lys Ala Leu Asp Asp
145                 150                 155                 160

Lys Val Val Glu Phe Lys Leu Lys Tyr Pro Phe Ala Leu Phe Lys Glu
                165                 170                 175

Arg Leu Thr Ile Val Lys Ile Val Pro Lys His Ile Val Glu Ala Gly
            180                 185                 190

Gln Ser Ala Phe Asp Ala Asn Pro Ile Gly Ser Gly Pro Tyr Arg Phe
        195                 200                 205

Val Ser Ala Thr Lys Asp Asp Arg Ile Val Phe Ala Ala Asn Pro Ala
210                 215                 220

Tyr Asn Gly Ile Tyr Pro Ala Lys Val Glu Lys Met Thr Trp Phe Leu
225                 230                 235                 240

Leu Ala Asp Asp Ala Ala Arg Val Thr Ala Gln Glu Ser Gly Arg Ile
                245                 250                 255

Gln Ala Met Glu Ser Val Pro Tyr Leu Asp Ala Gln Arg Leu Lys Arg
            260                 265                 270

Lys Thr Glu Val Gln Pro Val Gln Ser Phe Gly Leu Leu Phe Leu Met
        275                 280                 285

Phe Asn Cys Glu Lys Ala Pro Phe Asn Asn Pro Lys Val Arg Gln Ala
    290                 295                 300

Leu His Tyr Ala Ile Asp Thr Gln Lys Leu Ile Asp Ile Ala Phe Leu
305                 310                 315                 320
```

```
Gly Asn Ala Lys Ala Thr Ser Tyr Val Gln Asp Thr His Pro Asp
                325                 330                 335

Tyr Val Lys Ala Thr Ser Gln Tyr Asp Phe Asp Lys Ala Lys Ala Glu
            340                 345                 350

Ala Leu Leu Lys Glu Ala Gly Val Thr Glu Leu Lys Phe Gln Leu Leu
                355                 360                 365

Ser Thr Asp His Thr Trp Val Lys Glu Cys Ala Pro Leu Ile Leu Glu
            370                 375                 380

Ser Trp Asn Ala Leu Lys Gly Val Lys Ala Thr Leu Gln His Leu Gln
385                 390                 395                 400

Ser Gly Ala Leu Tyr Gly Ala His Val Asp Lys Gly Asn Phe Glu Val
                405                 410                 415

Val Ile Ala Pro Gly Asp Pro Ser Val Phe Gly Asn Asp Leu Asp Leu
            420                 425                 430

Leu Leu Ser Trp Trp Tyr Arg Gly Asp Val Trp Pro Lys Arg Arg Phe
                435                 440                 445

Arg Trp Ser Asn Thr Pro Glu Tyr Ala Glu Val Gln Lys Leu Leu Asp
            450                 455                 460

Glu Ala Val Arg Ala Lys Ser His Glu Glu Ala Lys Thr Ala Trp Thr
465                 470                 475                 480

Lys Ala Ile Asn Ile Ile Ala Glu Gln Val Pro Leu Tyr Pro Ile Ile
                485                 490                 495

His Arg Lys Leu Pro Thr Ala Trp Asn Ala Lys Ala Leu Thr Asp Phe
            500                 505                 510

Gln Pro Leu Pro Thr Thr Gly Leu Ser Phe Leu Gly Val Gly Arg Lys
                515                 520                 525

<210> SEQ ID NO 6
<211> LENGTH: 527
<212> TYPE: PRT
<213> ORGANISM: Mannheimia haemolytica

<400> SEQUENCE: 6

Met Lys Lys Gln Phe Glu His Asn Glu Ser Arg Arg Gly Phe Met Lys
1               5                   10                  15

Leu Ile Ala Gly Val Gly Ala Gly Met Ala Phe Ser Gly Thr Leu Gly
            20                  25                  30

Thr Phe Thr Pro Lys Ala Phe Ala Ala Pro Ala Ala Gly Ser Thr Ile
        35                  40                  45

Glu Ala Gly Ile Ala Tyr Pro Ile Ser Thr Gly Phe Asp Pro Leu Thr
    50                  55                  60

Ser Ser Gly Ala Ser Ser Met Ala Ala Asn Leu His Ile Phe Glu Gly
65                  70                  75                  80

Leu Val Asp Leu His Pro Ala Thr Arg Lys Pro Tyr Leu Ala Leu Ala
                85                  90                  95

Ala Ala Glu Pro Glu Lys Ile Asp Asp Val Thr Tyr Arg Ile Thr Leu
            100                 105                 110

Arg Asp Gly Ala Lys Phe His Asn Gly Asn Pro Val Thr Thr Glu Asp
        115                 120                 125

Val Val Tyr Ser Phe Glu Arg Val Leu Asp Pro Ala Lys Ala Ser Leu
    130                 135                 140

Phe Ala Gln Phe Ile Pro Phe Ile Asp Thr Val Lys Lys Val Asp Asp
145                 150                 155                 160

Lys Val Val Glu Phe Lys Leu Lys Tyr Pro Phe Ala Leu Phe Lys Glu
                165                 170                 175
```

```
Arg Leu Thr Ile Val Lys Ile Val Pro Lys Ala Val Glu Ala Gly
            180                 185                 190

Gln Ala Ala Phe Asp Ala Asn Pro Val Gly Thr Gly Pro Tyr Lys Phe
        195                 200                 205

Val Ser Ala Thr Lys Asp Asp Arg Ile Val Phe Glu Ala Phe Ala Asp
    210                 215                 220

Tyr Asn Gly Gly Tyr Pro Ala Gln Val Glu Lys Met Thr Trp Phe Leu
225                 230                 235                 240

Leu Ser Asp Asp Ala Ala Arg Val Thr Ala Gln Glu Ser Gly Arg Val
            245                 250                 255

Gln Ala Ile Glu Ser Val Pro Tyr Leu Asp Ala Glu Arg Leu Lys Arg
        260                 265                 270

Lys Gly Thr Val Glu Ser Val Gln Ser Phe Gly Leu Leu Phe Leu Met
    275                 280                 285

Phe Asn Cys Glu Lys Ala Pro Phe Asn Asn Pro Lys Val Arg Gln Ala
290                 295                 300

Leu His Tyr Gly Leu Asp Thr Gln Lys Leu Ile Asp Val Val Phe Leu
305                 310                 315                 320

Gly Asn Ala Lys Ala Ala Thr Ser Tyr Val Gln Asp Thr His Pro Asp
            325                 330                 335

Tyr Val Lys Ala Asn Ser Gln Tyr Asp Phe Asp Lys Ala Lys Ala Glu
        340                 345                 350

Ala Leu Leu Ala Glu Ala Gly Val Thr Glu Leu Lys Phe Glu Leu Leu
    355                 360                 365

Ala Thr Asp His Ser Trp Val Lys Glu Cys Ala Pro Leu Ile Leu Glu
370                 375                 380

Ser Trp Asn Ser Leu Lys Gly Val Lys Val Ser Leu Lys His Leu Gln
385                 390                 395                 400

Ser Gly Ala Leu Tyr Gly Thr His Val Asp Lys Gly Ala Tyr Glu Val
            405                 410                 415

Val Ile Ala Pro Gly Asp Pro Ser Val Phe Gly Asn Asp Leu Asp Leu
        420                 425                 430

Leu Leu Ser Trp Trp Tyr Arg Gly Asp Val Trp Pro Lys Arg Arg Phe
    435                 440                 445

Arg Trp Ser Glu Thr Ala Glu Tyr Ala Glu Val Gln Lys Leu Leu Asp
450                 455                 460

Glu Ala Ala Lys Asn Pro Ala Ala Ser Lys Glu Ala Trp Ala Lys Ala
465                 470                 475                 480

Ile Asn Ile Ile Ala Glu Gln Val Pro Leu Tyr Pro Ile Ile His Arg
            485                 490                 495

Lys Leu Pro Thr Ala Trp Asn Asp Lys Ala Leu Thr Gly Phe Gln Pro
        500                 505                 510

Leu Pro Thr Thr Gly Met Ser Phe Ile Gly Val Gly Arg Ala Lys
    515                 520                 525
```

<210> SEQ ID NO 7
<211> LENGTH: 20
<212> TYPE: DNA
<213> ORGANISM: artificial
<220> FEATURE:
<223> OTHER INFORMATION: synthetic oligonucleotide primer

<400> SEQUENCE: 7
cggcttacac caatgaatga        20

```
<210> SEQ ID NO 8
<211> LENGTH: 20
<212> TYPE: DNA
<213> ORGANISM: artificial
<220> FEATURE:
<223> OTHER INFORMATION: synthetic oligonucleotide primer

<400> SEQUENCE: 8
gtgttggtgc tggtttagca                                              20

<210> SEQ ID NO 9
<211> LENGTH: 1581
<212> TYPE: DNA
<213> ORGANISM: Haemophilus parasuis

<400> SEQUENCE: 9
atgaccaaac atttcgaaca caacgaatct cgtcgcggtt ttatgaaact ggtggcgggt    60
gttggtgcag gtctggcatt ctctggtagt atcggcacct ttgcctctca ggcgtatgcg   120
gccccggcca aggtagtac cattgaaacg ggcatcgcat acccgattag caccggtttc    180
gatccgatga gctctacggg cgccagtagc atggcagcga atattcatat ctttgaaggc   240
ctggtggatc tgcacccggc aacccgtcag ccgtatctgg cactggccgc aaaagaaccg   300
gaaaaagtgg atgatgttac ctaccgtatt acgctgcgcg atggtgcggt gtttcataac   360
ggctctgcgg ttaccagtgc cgatgtggtt tttagcttcg aacgcgttct ggacccgaat   420
acgaaatctc tgtttgcgca gttcattccg tttatcaaaa gtgtgaccgc cgttgatcag   480
aaaacggtgg aattcaaact gaaatatccg ttcgcgctgt ttaaagaacg tctgaccatt   540
atcaaaatcg tgccgaaagc actgattgaa gcgcagggtc agagtgtttt tgatgcaaac   600
ccggcaggca ccggtccgta caaattcgtg agcgccgtta agatgatcg catcgtgttt    660 gaagcaaatc cggcgtatac gggtccgtac ccggcaaccg ttgaaaaaat gacgtggttc   720
ctgctgtttg atgatgcagc ccgtgtggca gcacaggaaa gcggtcgtgt gcaggcaatt   780
gaaaacgttc cgtatctgga tgcggatcgt ctgaaacgca agccgcagt ggaaagtgtt    840 cagagcttcg gtctgatctt cctgatgttt aattgcgaaa agccccgtt aacaataaa     900 aaagtgcgtc aggccctgca gtatgcaatt gatacccaga actggttga tgtggttttt    960 ctgggcaacg ccaaaccggc aaccagctac gtgcaggatt ctcatccgga ttatgtgaaa  1020
gcgagcacgg tttacgattt cgatccgaaa aaagcggccg cactgctgaa gaagcaggt   1080 gttgataaac tggaatttac cacgcgcagt accgcgcaca atgggtggt tgatagcgtg   1140 cagatgatcc tggaagattg gaacaaaatt ccgggcgtga agttacgaa tatcgcgagc   1200 cagtctccgt ataacgatgg tgtggatgcg ggcaatttcg aagttctgat tgccccgggt  1260
gatccgagcg tttttggcaa cgatctggat ctgctgctgt cttggtggta tcgtggcgat  1320
gtgtggccga aaaacgtttt tcgctggagc aatacccgg aatacgcgga agtgcagaaa   1380
ctgctggatg cggccgttgc agcgaaaacg ccggcggaag cccgtgaaat ctgggtaaa   1440 gcgattaaca ttatcgccga agaagccgca ctgtatccga ttatccaccg caaactgccg  1500
accgcatgga gcaataaagc gctggatggc ttcaaaccgc tgagtaccac gggtatgagc  1560
tttattggcg tgtctcgcaa a                                            1581

<210> SEQ ID NO 10
<211> LENGTH: 7
<212> TYPE: PRT
<213> ORGANISM: artificial
```

```
<220> FEATURE:
<223> OTHER INFORMATION: TEV protease cleavage site

<400> SEQUENCE: 10

Glu Asn Leu Tyr Phe Gln Gly
1               5

<210> SEQ ID NO 11
<211> LENGTH: 5
<212> TYPE: PRT
<213> ORGANISM: artificial
<220> FEATURE:
<223> OTHER INFORMATION: enterokinase protease cleavage site

<400> SEQUENCE: 11

Asp Asp Asp Asp Lys
1               5

<210> SEQ ID NO 12
<211> LENGTH: 550
<212> TYPE: PRT
<213> ORGANISM: artificial
<220> FEATURE:
<223> OTHER INFORMATION: sub-cloned polypeptide

<400> SEQUENCE: 12

Met Asn His Lys Val His His His His His Met Glu Leu Gly Thr
1               5                   10                  15

Glu Asn Leu Tyr Phe Gln Gly Met Thr Lys His Phe Glu His Asn Glu
                20                  25                  30

Ser Arg Arg Gly Phe Met Lys Leu Val Ala Gly Val Ala Gly Leu
        35                  40                  45

Ala Phe Ser Gly Ser Ile Gly Thr Phe Ala Ser Gln Ala Tyr Ala Ala
        50                  55                  60

Pro Ala Lys Gly Ser Thr Ile Glu Thr Gly Ile Ala Tyr Pro Ile Ser
65                  70                  75                  80

Thr Gly Phe Asp Pro Met Ser Ser Thr Gly Ala Ser Ser Met Ala Ala
                85                  90                  95

Asn Ile His Ile Phe Glu Gly Leu Val Asp Leu His Pro Ala Thr Arg
                100                 105                 110

Gln Pro Tyr Leu Ala Leu Ala Ala Lys Glu Pro Glu Lys Val Asp Asp
        115                 120                 125

Val Thr Tyr Arg Ile Thr Leu Arg Asp Gly Ala Val Phe His Asn Gly
        130                 135                 140

Ser Ala Val Thr Ser Ala Asp Val Val Phe Ser Phe Glu Arg Val Leu
145                 150                 155                 160

Asp Pro Asn Thr Lys Ser Leu Phe Ala Gln Phe Ile Pro Phe Ile Lys
                165                 170                 175

Ser Val Thr Ala Val Asp Gln Lys Thr Val Glu Phe Lys Leu Lys Tyr
                180                 185                 190

Pro Phe Ala Leu Phe Lys Glu Arg Leu Thr Ile Ile Lys Ile Val Pro
        195                 200                 205

Lys Ala Leu Ile Glu Ala Gln Gly Gln Ser Val Phe Asp Ala Asn Pro
210                 215                 220

Ala Gly Thr Gly Pro Tyr Lys Phe Val Ser Ala Val Lys Asp Asp Arg
225                 230                 235                 240

Ile Val Phe Glu Ala Asn Pro Ala Tyr Thr Gly Pro Tyr Pro Ala Thr
                245                 250                 255
```

Val Glu Lys Met Thr Trp Phe Leu Leu Phe Asp Asp Ala Ala Arg Val
            260                 265                 270

Ala Ala Gln Glu Ser Gly Arg Val Gln Ala Ile Glu Asn Val Pro Tyr
        275                 280                 285

Leu Asp Ala Asp Arg Leu Lys Arg Lys Ala Ala Val Glu Ser Val Gln
290                 295                 300

Ser Phe Gly Leu Ile Phe Leu Met Phe Asn Cys Glu Lys Ala Pro Phe
305                 310                 315                 320

Asn Asn Lys Lys Val Arg Gln Ala Leu Gln Tyr Ala Ile Asp Thr Gln
                325                 330                 335

Lys Leu Val Asp Val Val Phe Leu Gly Asn Ala Lys Pro Ala Thr Ser
            340                 345                 350

Tyr Val Gln Asp Ser His Pro Asp Tyr Val Lys Ala Ser Thr Val Tyr
        355                 360                 365

Asp Phe Asp Pro Lys Lys Ala Ala Leu Leu Lys Glu Ala Gly Val
370                 375                 380

Asp Lys Leu Glu Phe Thr Thr Arg Ser Thr Ala His Lys Trp Val Val
385                 390                 395                 400

Asp Ser Val Gln Met Ile Leu Glu Asp Trp Asn Lys Ile Pro Gly Val
                405                 410                 415

Lys Val Thr Asn Ile Ala Ser Gln Ser Pro Tyr Asn Asp Gly Val Asp
            420                 425                 430

Ala Gly Asn Phe Glu Val Leu Ile Ala Pro Gly Asp Pro Ser Val Phe
        435                 440                 445

Gly Asn Asp Leu Asp Leu Leu Ser Trp Trp Tyr Arg Gly Asp Val
450                 455                 460

Trp Pro Lys Lys Arg Phe Arg Trp Ser Asn Thr Pro Glu Tyr Ala Glu
465                 470                 475                 480

Val Gln Lys Leu Leu Asp Ala Val Ala Ala Lys Thr Pro Ala Glu
                485                 490                 495

Ala Arg Glu Ile Trp Gly Lys Ala Ile Asn Ile Ala Glu Glu Ala
            500                 505                 510

Ala Leu Tyr Pro Ile Ile His Arg Lys Leu Pro Thr Ala Trp Ser Asn
        515                 520                 525

Lys Ala Leu Asp Gly Phe Lys Pro Leu Ser Thr Thr Gly Met Ser Phe
530                 535                 540

Ile Gly Val Ser Arg Lys
545                 550

<210> SEQ ID NO 13
<211> LENGTH: 685
<212> TYPE: PRT
<213> ORGANISM: artificial
<220> FEATURE:
<223> OTHER INFORMATION: sub-cloned polypeptide

<400> SEQUENCE: 13

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

-continued

```
Pro Gly Thr Ala Pro Lys Tyr Gly Ile Arg Gly Ile Pro Thr Leu Leu
 65                  70                  75                  80

Leu Phe Lys Asn Gly Glu Val Ala Ala Thr Lys Val Gly Ala Leu Ser
                 85                  90                  95

Lys Gly Gln Leu Lys Glu Phe Leu Asp Ala Asn Leu Ala Gly Ser Gly
            100                 105                 110

Ser Gly His Met His His His His His His Ser Ser Gly Leu Val Pro
            115                 120                 125

Arg Gly Ser Gly Met Lys Glu Thr Ala Ala Ala Lys Phe Glu Arg Gln
        130                 135                 140

His Met Asp Ser Pro Asp Leu Gly Thr Asp Asp Asp Lys Met Thr
145                 150                 155                 160

Lys His Phe Glu His Asn Glu Ser Arg Arg Gly Phe Met Lys Leu Val
                165                 170                 175

Ala Gly Val Gly Ala Gly Leu Ala Phe Ser Gly Ser Ile Gly Thr Phe
            180                 185                 190

Ala Ser Gln Ala Tyr Ala Ala Pro Ala Lys Gly Ser Thr Ile Glu Thr
        195                 200                 205

Gly Ile Ala Tyr Pro Ile Ser Thr Gly Phe Asp Pro Met Ser Ser Thr
    210                 215                 220

Gly Ala Ser Ser Met Ala Ala Asn Ile His Ile Phe Glu Gly Leu Val
225                 230                 235                 240

Asp Leu His Pro Ala Thr Arg Gln Pro Tyr Leu Ala Leu Ala Ala Lys
                245                 250                 255

Glu Pro Glu Lys Val Asp Asp Val Thr Tyr Arg Ile Thr Leu Arg Asp
            260                 265                 270

Gly Ala Val Phe His Asn Gly Ser Ala Val Thr Ser Ala Asp Val Val
        275                 280                 285

Phe Ser Phe Glu Arg Val Leu Asp Pro Asn Thr Lys Ser Leu Phe Ala
    290                 295                 300

Gln Phe Ile Pro Phe Ile Lys Ser Val Thr Ala Val Asp Gln Lys Thr
305                 310                 315                 320

Val Glu Phe Lys Leu Lys Tyr Pro Phe Ala Leu Phe Lys Glu Arg Leu
                325                 330                 335

Thr Ile Ile Lys Ile Val Pro Lys Ala Leu Ile Glu Ala Gln Gly Gln
            340                 345                 350

Ser Val Phe Asp Ala Asn Pro Ala Gly Thr Gly Pro Tyr Lys Phe Val
        355                 360                 365

Ser Ala Val Lys Asp Asp Arg Ile Val Phe Glu Ala Asn Pro Ala Tyr
    370                 375                 380

Thr Gly Pro Tyr Pro Ala Thr Val Glu Lys Met Thr Trp Phe Leu Leu
385                 390                 395                 400

Phe Asp Asp Ala Ala Arg Val Ala Ala Gln Glu Ser Gly Arg Val Gln
                405                 410                 415

Ala Ile Glu Asn Val Pro Tyr Leu Asp Ala Asp Arg Leu Lys Arg Lys
            420                 425                 430

Ala Ala Val Glu Ser Val Gln Ser Phe Gly Leu Ile Phe Leu Met Phe
        435                 440                 445

Asn Cys Glu Lys Ala Pro Phe Asn Asn Lys Lys Val Arg Gln Ala Leu
    450                 455                 460

Gln Tyr Ala Ile Asp Thr Gln Lys Leu Val Asp Val Val Phe Leu Gly
465                 470                 475                 480
```

```
Asn Ala Lys Pro Ala Thr Ser Tyr Val Gln Asp Ser His Pro Asp Tyr
                485                 490                 495

Val Lys Ala Ser Thr Val Tyr Asp Phe Asp Pro Lys Lys Ala Ala Ala
            500                 505                 510

Leu Leu Lys Glu Ala Gly Val Asp Lys Leu Glu Phe Thr Thr Arg Ser
            515                 520                 525

Thr Ala His Lys Trp Val Val Asp Ser Val Gln Met Ile Leu Glu Asp
            530                 535                 540

Trp Asn Lys Ile Pro Gly Val Lys Val Thr Asn Ile Ala Ser Gln Ser
545                 550                 555                 560

Pro Tyr Asn Asp Gly Val Asp Ala Gly Asn Phe Glu Val Leu Ile Ala
                565                 570                 575

Pro Gly Asp Pro Ser Val Phe Gly Asn Asp Leu Asp Leu Leu Leu Ser
            580                 585                 590

Trp Trp Tyr Arg Gly Asp Val Trp Pro Lys Lys Arg Phe Arg Trp Ser
            595                 600                 605

Asn Thr Pro Glu Tyr Ala Glu Val Gln Lys Leu Leu Asp Ala Ala Val
            610                 615                 620

Ala Ala Lys Thr Pro Ala Glu Ala Arg Glu Ile Trp Gly Lys Ala Ile
625                 630                 635                 640

Asn Ile Ile Ala Glu Glu Ala Ala Leu Tyr Pro Ile Ile His Arg Lys
                645                 650                 655

Leu Pro Thr Ala Trp Ser Asn Lys Ala Leu Asp Gly Phe Lys Pro Leu
            660                 665                 670

Ser Thr Thr Gly Met Ser Phe Ile Gly Val Ser Arg Lys
            675                 680                 685

<210> SEQ ID NO 14
<211> LENGTH: 775
<212> TYPE: PRT
<213> ORGANISM: artificial
<220> FEATURE:
<223> OTHER INFORMATION: sub-cloned polypeptide

<400> SEQUENCE: 14

Met Ser Gly Ser His His His His His Ser Ser Gly Met Ser Pro
1               5                   10                  15

Ile Leu Gly Tyr Trp Lys Ile Lys Gly Leu Val Gln Pro Thr Arg Leu
            20                  25                  30

Leu Leu Glu Tyr Leu Glu Glu Lys Tyr Glu Glu His Leu Tyr Glu Arg
            35                  40                  45

Asp Glu Gly Asp Lys Trp Arg Asn Lys Lys Phe Glu Leu Gly Leu Glu
        50                  55                  60

Phe Pro Asn Leu Pro Tyr Tyr Ile Asp Gly Asp Val Lys Leu Thr Gln
65                  70                  75                  80

Ser Met Ala Ile Ile Arg Tyr Ile Ala Asp Lys His Asn Met Leu Gly
                85                  90                  95

Gly Cys Pro Lys Glu Arg Ala Glu Ile Ser Met Leu Glu Gly Ala Val
            100                 105                 110

Leu Asp Ile Arg Tyr Gly Val Ser Arg Ile Ala Tyr Ser Lys Asp Phe
            115                 120                 125

Glu Thr Leu Lys Val Asp Phe Leu Ser Lys Leu Pro Glu Met Leu Lys
        130                 135                 140

Met Phe Glu Asp Arg Leu Cys His Lys Thr Tyr Leu Asn Gly Asp His
145                 150                 155                 160
```

```
Val Thr His Pro Asp Phe Met Leu Tyr Asp Ala Leu Asp Val Val Leu
            165                 170                 175

Tyr Met Asp Pro Met Cys Leu Asp Ala Phe Pro Lys Leu Val Cys Phe
            180                 185                 190

Lys Lys Arg Ile Glu Ala Ile Pro Gln Ile Asp Lys Tyr Leu Lys Ser
            195                 200                 205

Ser Lys Tyr Ile Ala Trp Pro Leu Gln Gly Trp Gln Ala Thr Phe Gly
            210                 215                 220

Gly Gly Asp His Pro Pro Lys Ser Asp Leu Gly His Thr Gly His Arg
225                 230                 235                 240

Ser Gly Thr Asp Asp Asp Lys Met Thr Lys His Phe Glu His Asn
            245                 250                 255

Glu Ser Arg Arg Gly Phe Met Lys Leu Val Ala Gly Val Gly Ala Gly
            260                 265                 270

Leu Ala Phe Ser Gly Ser Ile Gly Thr Phe Ala Ser Gln Ala Tyr Ala
            275                 280                 285

Ala Pro Ala Lys Gly Ser Thr Ile Glu Thr Gly Ile Ala Tyr Pro Ile
            290                 295                 300

Ser Thr Gly Phe Asp Pro Met Ser Ser Thr Gly Ala Ser Ser Met Ala
305                 310                 315                 320

Ala Asn Ile His Ile Phe Glu Gly Leu Val Asp Leu His Pro Ala Thr
            325                 330                 335

Arg Gln Pro Tyr Leu Ala Leu Ala Lys Glu Pro Glu Lys Val Asp
            340                 345                 350

Asp Val Thr Tyr Arg Ile Thr Leu Arg Asp Gly Ala Val Phe His Asn
            355                 360                 365

Gly Ser Ala Val Thr Ser Ala Asp Val Val Phe Ser Phe Glu Arg Val
            370                 375                 380

Leu Asp Pro Asn Thr Lys Ser Leu Phe Ala Gln Phe Ile Pro Phe Ile
385                 390                 395                 400

Lys Ser Val Thr Ala Val Asp Gln Lys Thr Val Glu Phe Lys Leu Lys
            405                 410                 415

Tyr Pro Phe Ala Leu Phe Lys Glu Arg Leu Thr Ile Ile Lys Ile Val
            420                 425                 430

Pro Lys Ala Leu Ile Glu Ala Gln Gly Gln Ser Val Phe Asp Ala Asn
            435                 440                 445

Pro Ala Gly Thr Gly Pro Tyr Lys Phe Val Ser Ala Val Lys Asp Asp
            450                 455                 460

Arg Ile Val Phe Glu Ala Asn Pro Ala Tyr Thr Gly Pro Tyr Pro Ala
465                 470                 475                 480

Thr Val Glu Lys Met Thr Trp Phe Leu Leu Phe Asp Asp Ala Ala Arg
            485                 490                 495

Val Ala Ala Gln Glu Ser Gly Arg Val Gln Ala Ile Glu Asn Val Pro
            500                 505                 510

Tyr Leu Asp Ala Asp Arg Leu Lys Arg Lys Ala Ala Val Glu Ser Val
            515                 520                 525

Gln Ser Phe Gly Leu Ile Phe Leu Met Phe Asn Cys Glu Lys Ala Pro
            530                 535                 540

Phe Asn Asn Lys Lys Val Arg Gln Ala Leu Gln Tyr Ala Ile Asp Thr
545                 550                 555                 560

Gln Lys Leu Val Asp Val Val Phe Leu Gly Asn Ala Lys Pro Ala Thr
            565                 570                 575
```

-continued

```
Ser Tyr Val Gln Asp Ser His Pro Asp Tyr Val Lys Ala Ser Thr Val
            580                 585                 590

Tyr Asp Phe Asp Pro Lys Lys Ala Ala Leu Leu Lys Glu Ala Gly
        595             600             605

Val Asp Lys Leu Glu Phe Thr Thr Arg Ser Thr Ala His Lys Trp Val
        610             615             620

Val Asp Ser Val Gln Met Ile Leu Glu Asp Trp Asn Lys Ile Pro Gly
625                 630                 635                 640

Val Lys Val Thr Asn Ile Ala Ser Gln Ser Pro Tyr Asn Asp Gly Val
                645             650                 655

Asp Ala Gly Asn Phe Glu Val Leu Ile Ala Pro Gly Asp Pro Ser Val
            660             665             670

Phe Gly Asn Asp Leu Asp Leu Leu Ser Trp Trp Tyr Arg Gly Asp
        675             680             685

Val Trp Pro Lys Lys Arg Phe Arg Trp Ser Asn Thr Pro Glu Tyr Ala
    690             695             700

Glu Val Gln Lys Leu Leu Asp Ala Ala Val Ala Ala Lys Thr Pro Ala
705             710             715             720

Glu Ala Arg Glu Ile Trp Gly Lys Ala Ile Asn Ile Ile Ala Glu Glu
            725             730             735

Ala Ala Leu Tyr Pro Ile Ile His Arg Lys Leu Pro Thr Ala Trp Ser
            740             745             750

Asn Lys Ala Leu Asp Gly Phe Lys Pro Leu Ser Thr Thr Gly Met Ser
        755             760             765

Phe Ile Gly Val Ser Arg Lys
770                 775
```